US009110064B2

(12) United States Patent
Braun et al.

(10) Patent No.: US 9,110,064 B2
(45) **Date of Patent: *Aug. 18, 2015**

(54) METHODS FOR DIAGNOSIS AND TREATMENT OF ENDOMETRIAL CANCER

(75) Inventors: Jonathan Braun, Tarzana, CA (US); Madhuri Wadehra, Fontana, CA (US); Sathima Natarajan, Los Angeles, CA (US); Robert Soslow, New York, NY (US)

(73) Assignees: THE REGENTS OF THE UNIVERSITY OF CALIFORNIA, Oakland, CA (US); MEMORIAL SLOAN KETTERING CANCER CENTER, New York, NY (US)

( * ) Notice: Subject to any disclaimer, the term of this patent is extended or adjusted under 35 U.S.C. 154(b) by 160 days.

This patent is subject to a terminal disclaimer.

(21) Appl. No.: 13/339,247

(22) Filed: Dec. 28, 2011

(65) Prior Publication Data

US 2012/0264620 A1 Oct. 18, 2012

Related U.S. Application Data

(63) Continuation of application No. 11/884,806, filed as application No. PCT/US2006/007180 on Feb. 28, 2006, now abandoned.

(60) Provisional application No. 60/657,607, filed on Feb. 28, 2005.

(51) Int. Cl.
*G01N 33/53* (2006.01)
*G01N 33/567* (2006.01)
*G01N 33/574* (2006.01)
*C12Q 1/68* (2006.01)

(52) U.S. Cl.
CPC ........ *G01N 33/57407* (2013.01); *C12Q 1/6886* (2013.01); *G01N 33/57442* (2013.01); *C12Q 2600/118* (2013.01); *C12Q 2600/136* (2013.01); *C12Q 2600/158* (2013.01); *G01N 2500/02* (2013.01); *G01N 2500/10* (2013.01)

(58) Field of Classification Search
None
See application file for complete search history.

(56) References Cited

U.S. PATENT DOCUMENTS

| | | | | |
|---|---|---|---|---|
| 5,264,188 | A | 11/1993 | Lew | |
| 5,270,163 | A | 12/1993 | Gold et al. | |
| 5,288,514 | A | 2/1994 | Ellman | |
| 5,475,096 | A | 12/1995 | Gold et al. | |
| 5,506,337 | A | 4/1996 | Summerton et al. | |
| 5,519,134 | A | 5/1996 | Acevedo et al. | |
| 5,525,735 | A | 6/1996 | Gallop et al. | |
| 5,539,083 | A | 7/1996 | Cook et al. | |
| 5,549,974 | A | 8/1996 | Holmes | |
| 5,569,588 | A | 10/1996 | Ashby et al. | |
| 5,593,853 | A | 1/1997 | Chen et al. | |
| 5,786,362 | A | 7/1998 | Krongrad | |
| 6,413,245 | B1 | 7/2002 | Yaacobi et al. | |
| 6,506,781 | B1 | 1/2003 | Cobb et al. | |
| 6,750,015 | B2 | 6/2004 | Horwitz et al. | |
| 6,794,378 | B2 | 9/2004 | Iino et al. | |
| 7,229,770 | B1 * | 6/2007 | Price et al. | 435/7.1 |
| 7,288,531 | B2 | 10/2007 | Pal et al. | |
| 7,304,042 | B2 | 12/2007 | Pal et al. | |
| 7,345,027 | B2 | 3/2008 | Tolentino et al. | |
| 7,504,385 | B2 | 3/2009 | Binetti et al. | |
| 7,511,025 | B2 | 3/2009 | Wyatt et al. | |
| 7,517,865 | B2 | 4/2009 | Meyers | |
| 7,521,431 | B2 | 4/2009 | Reich et al. | |
| 7,585,848 | B2 | 9/2009 | Masuda et al. | |
| 7,592,325 | B2 | 9/2009 | Jimenez et al. | |
| 7,629,323 | B2 | 12/2009 | Surmeier et al. | |
| 7,638,482 | B2 | 12/2009 | LaVallie et al. | |
| 2003/0228305 | A1 * | 12/2003 | Frantz et al. | 424/141.1 |
| 2004/0175385 | A1 | 9/2004 | Marks et al. | |
| 2005/0244463 | A1 | 11/2005 | Huang et al. | |
| 2006/0062785 | A1 | 3/2006 | Freson et al. | |
| 2007/0065889 | A1 | 3/2007 | Roberts et al. | |
| 2013/0004493 | A1 | 1/2013 | Gordon et al. | |

FOREIGN PATENT DOCUMENTS

| | | |
|---|---|---|
| EP | 0430539 A2 | 6/1991 |
| EP | 0488401 A1 | 6/1992 |
| JP | 2009-531463 A | 9/2009 |
| JP | 2013-511543 A | 4/2013 |
| WO | WO 91/19735 | 12/1991 |
| WO | WO 91/19813 | 12/1991 |
| WO | WO 92/00091 | 1/1992 |
| WO | WO 93/20242 | 10/1993 |
| WO | WO 03/057160 | 7/2003 |
| WO | WO 2005/055808 | 6/2005 |
| WO | WO 2006/094014 | 9/2006 |

(Continued)

OTHER PUBLICATIONS

Wadehra, ProQuest Dissertation and Theses, 2002.*

Abrami et al., "Cross-talk between Caveolae and Glycosylphophatidylinositol-rich Domains" *Journal of Biol. Chemistry*, vol. 276, No. 33, pp. 30729-30736 (2001).

Agrawal et al., "Antisense therapeutics: is it as simple as complementary base recognition?" *Molecular Medicine Today*, vol. 6, pp. 72-81 (2000).

(Continued)

*Primary Examiner* — Hong Sang
(74) *Attorney, Agent, or Firm* — Morgan, Lewis & Bockius LLP; Annette S. Parent

(57) ABSTRACT

The present invention discloses methods of using epithelial membrane protein 2 (EMP2) as a biomarker for stratification of endometrial premalignancy, diagnosing, staging and imaging of endometrial neoplasia. Further, methods for identifying pharmaceutical/therapeutic modalities are described, including compositions which modulate glycolipid-enriched lipid raft microdomains (GEMs).

3 Claims, 15 Drawing Sheets

(56) References Cited

FOREIGN PATENT DOCUMENTS

| | | |
|---|---|---|
| WO | WO 2007/115045 | 10/2007 |
| WO | WO 2009/048980 | 4/2009 |
| WO | WO 2011/063161 | 5/2011 |

OTHER PUBLICATIONS

Bersinger et al., "Production of endometrial placental protein 14 and prolactin by cultured endometrial explants after collagenase and freeze/thaw treatment, and in response to progesterone" *Early Pregnancy: Biology and Medicine*, vol. 1, pp. 134-140 (1995).
Colman, "Effects of amino acid sequence changes on antibody-antigen interactions" *Research in Immunology*, vol. 145, pp. 33-36 (1994).
Gura, "Systems for Identifying New Drugs Are Often Faulty" *Science*, vol. 278, pp. 1041-1042 (1997).
Jain, "Barriers to Drug Delivery in Solid Tumors" *Scientific American*, July, pp. 58-65 (1994).
Jen et al., "Suppression of Gene Expression by Targeted Disruption of Messenger RNA: Available Options and Current Strategies" *Stem Cells*, vol. 18, pp. 307-319 (2000).
Leitinger and Hogg, "The involvement of lipid rafts in the regulation of integrin function" *Journal of Cell Science*, vol. 115, No. 5, pp. 963-972 (2002).
Melkonian et al., "Role of Lipid Modifications in Targeting Proteins to Detergent-resistant Membrane Rafts" *Journal of Biol. Chemistry*, vol. 276, No. 6, pp. 3910-3917 (1999).
Moffett et al., "Lipid-dependent Targeting of G Proteins into Rafts" *Journal of Biol. Chemistry*, vol. 275, No. 3, pp. 2191-2198 (2000).
Mohan et al., "Characterization of the Epithelial Membrane Protein 2 in the Progression of Endometrial Adenocarcinoma" *Modern Pathology*, Jan. 18 (Supp.1), p. 196A (2005).
MSNBC News Services, "Mixed results on new cancer drug" Nov. 9, pp. 1-4 (2000).
Nichols et al., "Rapid Cycling of Lipid Raft Markers between the Cell Surface and Golgi Complex" *Journal of Cell Biology*, vol. 153, No. 3, pp. 529-541 (2001).
Niu et al., "Restricted expression pattern of the putative tumor suppressor gene, Epithelial Membrane Protein 2 in the eye" *Invest Ophthalmol Vis. Sci*. E-Abstract 2419 (2002).
Opalinska et al., "Nucleic-Acid Therapeutics: Basic Principles and Recent Applications" *Nature Reviews Drug Discovery*, vol. 1, pp. 503-514 (2002).
Pareek et al., "Detection and Processing of Peripheral Myelin Protein PMP22 in Cultured Schwann Cells" *Journal Biol. Chemistry*, vol. 268, No. 14, pp. 10372-10379 (1993).
Paul, Ed., "Fv Structure and Diversity in Three Dimensions" *Fundamental Immunology, Third Edition*, Raven Press, New York, Chapter 8, pp. 292-295 (1993).
Rudikoff et al., "Single amino acid substitution altering antigen-binding specificity" *Proc. Natl. Acad. Sci*., vol. 79, No. 6, pp. 1979-1983 (1982).
Shimazaki et al., "Diabodies Targeting Epithelial Membrane Protein 2 Reduce Tumorigencity of Human Endometrial Cancer Cell Lines" *Clin. Cancer Res*., vol. 14, No. 22, pp. 7367-7377 (2008).
Taylor et al., "Epithelial membrance protein-2 and epithelial membrane protein-3: two novel members of the peripheral myelin protein 22 gene family" *Gene*, vol. 175, pp. 115-120 (1996).
Wadehra et al., "Epithelial membrane protein-2 is expressed in discrete anatomical regions of the eye" *Exper. Mol. Patho*., vol. 74, pp. 106-112 (2003).
Wadehra et al., "The tetraspan protein EMP2 increases surface expression of class I major histocompatability complex proteins and susceptibility to CTL-mediated cell death" *Clinical Immunology*, vol. 107, pp. 129-136 (2003).
Wadehra et al., "The Tetraspan Protein EMP2 Modulates the Surface Expression of Caveolins and Glycosylphosphatidyl Inositol-linked Proteins" *Molecular Biology of the Cell*, vol. 15, pp. 2073-2083 (2004).
Wang et al., "Epithelial membrane protein 2, a 4-transmembrane protein that suppresses B-cell lymphoma tumorigencity" *Blood*, vol. 97, No. 12, pp. 3890-3895 (2001).
Amarzguioui, M. et al., "An algorithm for selection of functional siRNA sequences," *Biochemical and Biophysical Research Communications*, 316:1050-1058 (2004).
Anderson, E.M. et al., "Experimental validation of the importance of seed complement frequency to SiRNA specificity," *RNA*, 14:853-861 (2008).
Birmingham, A. et al., "3' UTR seed matches, but not overall identity, are associated with RNAi off-targets," *Nature Methods*, 3(3):199-204 (2006).
Carey, A.J. and Beagley, K.W., "Chlamydia trachomatis, a Hidden Epidemic: Effects on Femal Reproduction and Options for Treatment", *Am. J. Reprod. Immunol*., Abstract only (2010).
Chen, Y. et al., "RNAi for Treating Hepatitis B Viral Infection", *Pharmaceutical Research*, vol. 25, No. 1, pp. 72-86 (2008).
Cui, W. et al., "OptiRNAi, an RNAi design tool," *Computer Methods and Programs in Biomedicine*, 75:67-73 (2004).
Delevoye, C. et al., "SNARE Protein Mimicry by an Intracellular Bacterium", *PLOS Pathogens*, vol. 4, Issue 3, (2008).
Dudek, P., et al., TROD: T7 RNAi Oligo Designer, *Nucleic Acids Research* 32:W121-W123 (2004).
Elbashir, S.M. et al., "Analysis of gene function in somatic mammalian cells using small interfering RNAs," *Methods* 26:199-213 (2002).
Flynn, M. A. et al., Efficient delivery of small interfering RNA for inhibition of IL-12p40 expression in vivo, *Journal of Inflammation* 1:4 (2004).
Ge, Q. et al., "Use of siRNAs to prevent and treat influenza virus infection", *Virus Research*, vol. 102, pp. 37-42 (2004).
Henschel, A. et al., DEQOR: a web-based tool for the design and quality control of siRNAs, *Nucleic Acids Research* 32:W113-W120 (2004).
Hsieh, A. C. et al., "A library of siRNA duplexes targeting the phosphoinositide 3-kinase AT pathway: determinants of gene silencing for use in cell-based screens," *Nucleic Acids Research* 32(3):893-901 (2004).
Jackson, A. L., et al., "Position-specific chemical modification of siRNAs reduces 'off- target' transcript silencing," *RNA* 12:1197-1205 (2006).
Kim, B. et al., Inhibition of Ocular Angiogenesis by siRNA Targeting Vascular Endothelial Growth Factor Pathway Genes, *American Journal of Pathology* 165(6):2177-2185 (2004).
Lane, B. Josh et al., "Chlamydial Entry Involves TARP Binding of Guanine Nucleotide Exchange Factors", *PLOS Pathogens*, vol. 4, Issue 3 (2008).
Levenkova, N. et al., "Gene specific siRNA selector," *Bioinformatics* 20(3): 430-432 (2004).
Luo, K. Q. et al., "The gene-silencing efficiency of siRNA is strongly dependent on the local structure of mRNA at the targeted region," *Biochemical and Biophysical Research Communications* 318:303-310 (2004).
Ma, Z. et al., Cationic lipids enhance siRNA-mediated interferon response in mice, *Biochemical and Biophysical Research Communications* 330:755-759 (2005).
Milhavet, O. et al., "RNA Interference in Biology and Medicine," *Pharmacol Rev* 55:629-648 (2003).
Morales, S.A. et al., "FAK Activation and the Role of Epithelial Membrane Protein 2 (EMP2) in Collagen Gel Contraction", *Investigative Ophthalmology & Visual Science*, vol. 50, No. 1, pp. 462-469 (2009).
Morales, S. A., "Functional Consequences of Interactions between FAK and Epithelial Membrane Protein 2 (EMP2)," *IOVS*, 50(10):4949-4956 (2009).
Morrissey, D. V. et al., "Activity of Stabilized Short Interfering RNA in a Mouse Model of Hepatitis B Virus Replication," *Hepatology* 41(6):1349-1356 (2005).
Morrissey, D. V. et al., Potent and persistent in vivo anti-HBV activity of chemically modified siRNAs, *Nature Biology* 23(8):1002-1007 (2005).
Naito, Y. et al., "siDirect: highly effective, target-specific siRNA design software for mammalian RNA interference," *Nucleic Acids Research*, 32:W124-W129 (2004).

(56) References Cited

OTHER PUBLICATIONS

Pancoskca, P. et al., "Efficient RNA interference depends on global context of the target BF sequence: quantitative analysis of silencing efficiency using Eulerian graph representation of siRNA," *Nucleic Acids Research*, 32(4):1469-1479 (2004).
Reich, S. J. et al., "Small interfering RNA (siRNA) targeting VEGF effectively inhibits ocular neovascularization in a mouse model," *Molecular Vision*, 9:210-216 (2003).
Reynolds, A. et al., "Rational siRNA design for RNA interference," *Nature Biology* 22(3):326-330 (2004).
Rossi, J.J. et al., "A practical siRNA microbicide?" *Gene Therapy*, vol. 13, pp. 1493-1494 (2006).
Schiffelers, R. M. et al., "Cancer siRNA therapy by tumor selective delivery with ligand-targeted sterically stabilized nanoparticle," *Nucleic Acids Research*, 32(19):e149 (2004).
Schubert, S. et al., "Local RNA Target Structure Influences siRNA Efficacy: Systematic Analysis of Intentionally Designed Binding Regions", *J. Mol. Biol.*, vol. 348, pp. 883-893 (2005).
Shimazaki, K. et al., "Blockade of epithelial membrane protein 2 (EMP2) abrogates infection of *Chlamydia muridarum* murine genital infection model," *FEMS Immunol Med Microbiol* 1-10 (2008).
Shimazaki, K. et al., Epithelial membrane protein 2 modulates infectivity of *Chlamydia muridarum* (MoPn), *Microbes and Infection* 9:1003-1010 (2007).
Soutschek, J. et al., "Therapeutic silencing of an endogenous gene by systemic administration of modified siRNAs," *Nature*, 432:173-178 (2004).
Swanson, K. et al., "*Chlamydia trachomatis* Species-Specific Induction of Ezrin Tyrosine Phosphorylation Functions in Pathogen Entry", *Infection and Immunity*, vol. 75, No. 12, pp. 5669-5677 (2007).
Takasaki, S. et al., "An Effective Method for Selecting siRNA Target Sequences in Mammalian Cells," *Cell Cycle* 3(6):790-795 (2004).
Taxman, D. J. et al., "Criteria for effective design, construction, and gene knockdown by shRNA vectors," *BMC Biotechnology* 6:7 (2006).
Ui-Tei, K. et al., "Guidelines for the selection of highly effective siRNA sequences for mammalian and chick RNA interference," *Nucleic Acids Research* 32(3):936-948 (2004).
Verma, U. N. et al., "Small Interfering RNAs Directed against β-Catenin Inhibit the in Vitro and in Vivo Growth of Colon Cancer Cells," Clinical Cancer Research, 9:1291-1300 (2003).
Wadehra, M. et al., "The Tetraspan Protein Epithelial Membrane Protein-2 Interacts with $\beta_1$ Integrins and Regulates Adhesion", *The Journal of Biological Chemistry*, vol. 277, pp. 41094-41100 (2002).
Wadehra, M. et al., "Epithelial membrane protein-2 regulates surface expression of alphavbeta3 integrin in the endometrium", *Developmental Biology*, vol. 287, Issue 2, pp. 336-345 (2005).
Wadehra, M. et al., "Expression of Epithelial Membrane Protein-2 is Associated with Endometrial Adenocarcinoma of Unfavorable Outcome", *Cancer*, vol. 107(1): pp. 90-98 (2006).
Wang, L., et al., "A Web-based design center for vector-based siRNA and siRNA cassette," *Bioinformatics* 20( 11 ): 1818-1820 (2004).
Xia, H. et al., "siRNA-mediated gene silencing in vitro and in vivo," *Nature Biotechnology*, 20:1006-1010 (2002).
Yano, J. et al., "Antitumor Activity of Small Interfering RNA/ Cationic Liposome Complex in Mouse Models of Cancer," *Clinical Cancer Research* 10:7721-7726 (2004).
Yuan, B. et al., "siRNA Selection Server: an automated siRNA oligonucleotide prediction server," *Nucleic Acids Research*, 32:W130-W134 (2004).
Zhang, Y. et al., "Intravenous RNA Interference Gene Therapy Targeting the Human Epidermal Growth Factor Receptor Prolongs Survival in Intracranial Brain Cancer," *Clinical Cancer Research*, 10:3667-3677 (2004).
Altschul, S. et al., "Basic Local Alignment Tool", *J. Mol. Biol.*, 215:403-410 (1990).
Altschul, S. et al., "Gapped BLAST and PSI-BLAST: a new generation of protein database search programs", *Nucleic Acids Research*, 25:17 3389-3402 (1997).
Ambati, J., et al. "Age-related macular degeneration: etiology, pathogenesis, and therapeutic strategies." *Surv Ophthalmol.* 48:257-293 (2003).
Batzer, M. et al., "Enhanced evolutionary PCR using oligonucleotides with inosine at the 3'-terminus", *Nucleic Acids Res.*, 19:18 5081 (1991).
Boiko E.V. et al., "To the detection rate of Chlamydia infection in regmatogenous retinal detachment", Abstract, *Vestn Oftalmol*, vol. 124, No. 5, pp. 52-55 (2008).
Campbell et al., "Phosphate Ester Synthesis Using a Modified Mitsunobu Condensation", *J. Org. Chem.*, 59: 658 (1994).
Chan, A.M. et al., "Epithelial Membrane Protein 2 (EMP2) Modulates Hypoxia-Inducible Factor 1α(Hif-1α and VEGF Expression by ARPE-19 Cells", *IOVS*, vol. 53, Abstract 4778 (2012).
Chen, C. et al., "'Analogous' organic synthesis of small compound libraries: Validation of combinatorial chemistry in small-molecule synthesis", *J. Am. Chem. Soc.*, 116: 2661-2662 (1994).
Cho, C. et al., "An unnatural biopolymer", *Science* 261: 1303 (1993).
Connolly, D. et al., "Tumor vascular permeability factor stimulates endothelial cell growth and angiogenesis", J. Clin. Invest. 84: 1470-1478 (1989).
Connolly, D. et al., "Human vascular permeability factor. Isolation from U937 cells", J. Biol. Chem., 264: 20017-20024 (1989).
De Witt, S. Hobbs et al., "'Diversomers': An approach to nonpeptide, nonoligomeric chemical diversity", *Proc. Natl., Acad. Sci. USA*, 90: 6909-6913 (1993).
Dufner, P. et al., "Harnessing phage and ribosome display for antibody optimisation", *Trends in Biotechnology*, vol. 24: No. 11, pp. 523-529 (2006).
Dvorak, H.F., "Tumors: wounds that do not heal. Similarities between tumor stroma generation and wound healing", N. Engl. Journ. Med., 315: 1650-1659 (1986).
Friedlander, M. et al., "Definition of Two Angiogenic Pathways by Distict $\alpha_v$ Integrins", Science, vol. 270, pp. 1500-1502 (1995).
Gerhardinger et al., "Expression of vascular endothelial growth factor in the human retina and in nonproliferative diabetic retinopathy", *Am. J. Pathol.* 152: 1453-1462 (1998).
Hagihara, M. et al., "Vinylogous polypeptides: an alternative peptide backbone", *J. Am. Chem. Soc.*, 114: 6568 (1992).
Harrison, C., "Eye Diseases—Convenient leakage reduction," *Nature Reviews Drug Discovery*, vol. 7 (2008).
Henikoff S. and Henikoff, J., "Amino acid substitution matrices from protein blocks", *Proc. Natl., Acad. Sci., USA*, 89: 10915-10919 (1992).
Hirschmann, R. et al., "Nonpeptidal peptidomimetics with beta-D-glucose scaffolding. A partial somatostatin against bearing a close structural relationship to a potent, selective substance P antagonist." *J. Am. Chem, Soc.*, 114: 9217-9218 (1992).
Hughes, L. and Maurice, D., "A Fresh Look at Iontophoresis", Arch Ophthalmol, vol. 102, pp. 1825-1829 (1984).
Husain, D. et al. "Photodynamic therapy and digital angiography of experimental iris neovascularization using liposomal benzoporphyrin derivative", *Opthamology* 104: 1242-12450 (1997).
Kim, I. et al., "Constitutive expression of VEGF, VEGFR-1, and VEGFR-2 in normal eyes", *Invest. Opthalmol. Vis. Sci.* 40: 2115-2121 (1999).
Kliffen, M. et al., "Increased expression of angiogenic growth factors in age-related maculopathy", Br. J Opthalmol. 81: 154-162 (1997).
Kvanta, A. et al., "Subfoveal fibrovascular membranes in age-related macular degeneration express vascular endothelial growth factor", *Invest. Opthalmol. Vis. Sci.* 37: 1929-1934 (1996).
Lee, V. H. L. et al., "Review: Topical Ocular Drug Delivery: Recent Developments and Future Challenges", *Journal of Ocular Pharmacology*, vol. 2, No. 1, pp. 67-108 (1986).
Leung, D.W. et al., "Vascular endothelial growth factor is a secreted angiogenic mitogen", *Science* 246:1306-1309 (1989).
Liang et al. "Parallel Synthesis and Screening of a Solid Phase Carbohydrate Library," *Science* 274:1520-1522 (1996).
Lopez, P. et al,, "Transdifferentiated retinal pigment epithelial cells are immunoreactive for vascular endothelial growth factor in surgically excised age-related macular degeneration-related choroidal neovascular membranes", *Invest. Opthalmol. Vis. Sci.* 37: 855-868 (1996).

(56) References Cited

OTHER PUBLICATIONS

McCafferty, J. et al., "Phage antibodies: filamentous phage displaying antibody variable domains", *Nature*, 348: 552-554 (1990).
McConnell, V. et al., "Assessment of a putative locus for exudative age-related macular degeration on chromosome 16p", *J. Med. Genet.* 41: Supplement 1 (2004).
Miller, J.W. et al., "Vascular endothelial growth factor in ocular neovascularization and proliferative diabetic retinopathy", *Diabetes Metab. Rev*. 13: 37-50 (1997).
Mitra, S.K.,and Schlaepfer, D.D., "Integrin-regulated FAK-Src signaling in normal and cancdr cells", *Current Opinion in Cell Biology*, vol. 18, pp. 516-523 (2006).
Morales, S.A. et al., "Collagen gel contraction by ARPE-19 cells is mediated by a FAK-Src dependent pathway", *Experimental Eye Research*, vol. 85, pp. 790-798 (2007).
Morales, S.A. et al., "Novel Therapies to Reduce Proliferative Vitreoretinopathy, Evidence From an in vitro Model", *IOVS*, vol. 50, Abstract 2713 (2009).
Morales, S. et al., "Epithelial Membrane Protein 2 Controls VEGF Expression in ARPE-19 Cells", *IVOS*, 54: 2367-2372 (2013).
Ohtsuka, E. et al., "An Alternative Approach to Deoxyoligonucleotieds as Hybridization Probes by Insertion of Deoxyinosine at Ambiguous Codon Positions", *The Journal of Biol. Chem*., 260:5 2605-2608 (1985).
Olsen, T.W. et al., "Human scleral permeability. Effects of age, cryotherapy, transscleral diode laser, and surgical thinning", *Invest. Ophthalmol. Vis. Sci*. 36: 1893-1903 (1995).
Plouet, J. et al., "Isolation and characterization of a newly identified endothelial cell mitogen produced by AtT-20 cells", *EMBO J.*, 8:3801-3806 (1989).
Rosenthal, R. et al., "$Ca^{2+}$ channels in retinal pigment epithelial cells regulate vascular endothelial growth factor secretion rates in health and disease", *Molecular Vision*, vol. 13, pp. 443-456 (2007).
Rossolini, G. et al., "Use of deoxyinosine-containing primers vs degenerate primers for polymerase chain reaction based on ambiguous sequence information", *Mol. Cell. Probes*, 8:91-98 (1994).
Sathish, J. et al. "Challenges and approaches for the development of safer immunomodulatory biologics", *Nature Reviews*, vol. 12, pp. 306-324 (2013).
Scheppke, L. et al., "Retinal vascular permeability suppression by topical application of a novel VEGFR2/Src kinase inhibitor in mice and rabbits", *The Journal of Clinical Investigation*, vol. 118, No. 6, pp. 2337-2346 (2008).
Schwesinger, C. et al., "Intrachoroidal neovascularization in transgenic mice overexpressing vascular endothelial growth factor in the retinal pigment epithelium", *Am. J. Pathol*. 158: 1161-1172 (2001).
Shimazaki, K. et al., "Expression of Epithelial Membrane Protein 2 (EMP-2) Controls Chlamydia Infectivity", *IOVS*, vol. 46, Abstract 5074 (2005).
Sorbera, L.A. et al. "Treatment of Age-Related Macular Degeneration Humanized Monoclonal Anti-VEGF Antibodiy Angiogenesis Inhibitor", *Drugs of the Future*, 28: 541-545 (2003).
Sundaresan, G. et al., "$^{124}$I-Labeled Engineered Anti-CEA Minibodies and Diabodies Allow High-Contrast, Antigen-Specific Small-Animal PET Imaging of Xenografts in Athymic Mice", *Journal of Nuclear Medicine*, 44:12, 1962-1969 (2003).
Vaughan et al, "Human Antibodies with Sub-nanomolar Affinities Isolated from a Large Non-immunized Phage Display Library," *Nature Biotechnology* 14(3):309-314 (1996).
Witte, L. et al., "Monoclonal antibodies targeting the VEGF receptor-2 (Flk1/KDR) as an antiangiogenic theraeutic strategy", *Cancer and Metatasis Review*, 17: pp. 155-161 (1998).
Wu, A. and Senter, P., "Arming antibodies: prospects and challenges for immunoconjugates", *Nature Biotech*, 23:1, 1137-1146 (2005).
Yi, X. et al., "Vascular endothelial growth factor expression in choroidal neovascularization in rats", *Graefes Arch Clin Exp Opthalmol* 235: 313-319 (1997).
Yu, L. et al., "Interaction between Bevacizumab and Murine VEGF-A: A Reassessment", *IVOS*, 49:2, pp. 522-527 (2008).

* cited by examiner

FIG. 2B

SEQUENCE LISTING

```
<160> NUMBER OF SEQ ID NOS: 3

<210> SEQ ID NO 1
<211> LENGTH: 20
<212> TYPE: PRT
<213> ORGANISM: Artificial Sequence
<220> FEATURE:
<223> OTHER INFORMATION: Synthetic construct

<400> SEQUENCE: 1

Glu Asp Ile His Asp Lys Asn Ala Lys Phe Tyr Pro Val Thr Arg Glu
1               5                   10                  15

Gly Ser Tyr Gly
            20


<210> SEQ ID NO 2
<211> LENGTH: 4
<212> TYPE: PRT
<213> ORGANISM: Artificial Sequence
<220> FEATURE:
<223> OTHER INFORMATION: Synthetic construct

<400> SEQUENCE: 2

Gly Ser Gly Ser
1


<210> SEQ ID NO 3
<211> LENGTH: 18
<212> TYPE: PRT
<213> ORGANISM: Artificial Sequence
<220> FEATURE:
<223> OTHER INFORMATION: Synthetic construct

<400> SEQUENCE: 3

Gly Ser Thr Ser Gly Gly Gly Ser Gly Gly Gly Ser Gly Gly Gly Gly
1               5                   10                  15

Ser Ser
```

METHODS FOR DIAGNOSIS AND TREATMENT OF ENDOMETRIAL CANCER

CROSS REFERENCE TO RELATED APPLICATIONS

This application is a Continuation of U.S. patent application Ser. No. 11/884,806 filed on Oct. 9, 2008, and is a 35 USC 371 National Stage application of PCT International Application No. PCT/US2006/007180 filed Feb. 28, 2006 which claims the benefit under 35 USC 119(e) to U.S. Provisional Application No. 60/657,607 filed on Feb. 28, 2005, all which are incorporated herein by reference in their entirety.

STATEMENT OF GOVERNMENT SUPPORT

This invention was made with Government support under Grant No. HD048540 awarded by the National Institutes of Health. The Government has certain rights in this invention.

FIELD OF THE INVENTION

This invention relates in general to detecting and treating cancers and more specifically to detecting and treating endometrial cancer (EC).

BACKGROUND INFORMATION

Endometrial carcinoma (EC), the most common of the gynecological malignancies, has 39,000 new cases and 6,500 deaths yearly. Premalignancy (atypical hyperplasia) is poorly understood, and risk of recurrence and death is currently only stratafiable by grade and stage parameters.

Preliminary treatment for EC is surgical excision. However, recurrence is significant, and chemotherapeutic management is only beneficial in a subset of individuals. Thus, like most cancers, there is a need not only for new modalities of treatment, but also for better identification of the premalignant state, which may provide better opportunities for early intervention and novel treatment modalities.

Reported clinical experiences have established that the histopathologic finding of atypical endometrial hyperplasia identifies individuals at elevated risk for subsequent EC risk. However, such findings are not biddy predictive, indicating heterogeneity in this population with regard to malignant potential (e.g., a Pap test is helpful but undependable, since 30-40% of smears yield false-negative results).

Epithelial Membrane Protein 2 (EMP2), which is expressed in the endometrium, is a four transmembrane protein which plays a critical role in selective receptor trafficking of a variety of proteins and glycolipids, effecting transfer from the post-Golgi endosomal compartment to the plasma membrane, including the transfer of molecules important in growth control, invasion, and metastasis. Accordingly, modulation of EMP2 expression and localization causes pleiotropic changes in the plasma membrane of selected members of several classes of molecules, including integrins, MHC class I and other immunoglobulin superfamily members (e.g., CD54), and GPI-linked proteins. Moreover, EMP2 mediates trafficking of these molecules to glycolipid-enriched lipid raft microdomains (GEMS). GEMs are cholesterol rich microdomains on the plasma membrane, and are associated with the sorting of proteins from the Golgi complex to the plasma membrane. At the plasma membrane, GEMs are thought to be important for receptor complexing and resultant signal transduction. It is possible that cells which utilize distinct GEMSs may permit separate assembly and regulation of distinct subsets of receptosomes.

With such profound consequences, disorders of EMP2 regulation may be a mode of pathogenesis, where alterations in physiologic regulation of EMP2 compartmentalization leads to neoplastic transformation.

SUMMARY OF THE INVENTION

The present invention relates to alterations in endothelial membrane protein 2 (EMP2) expression and disorders of EMP2 regulation which play a role in the pathogenesis of endometrial premalignancies, and ultimately in the development of endometrial cancer (EC). By correlating alterations in the expression of EMP2 with disease status, EMP2 is disclosed as a useful biological marker for diagnosis, staging, imaging, and as a therapeutic target for the treatment of the premalignant endometrial phenotype and EC.

In one embodiment, a method is disclosed for determining the likelihood of a group of endometrial cells becoming cancerous, including determining the level of endothelial membrane protein 2 (EMP2) polypeptide or polynucleotide in a test sample, where increased levels of EMP2 polypeptide or polynucleotide in the test sample relative to a control sample correlates with the endometrial cells having an increased likelihood of becoming cancerous. Thus, the invention provides a method for determining whether a subject has or is at risk of having EC.

In a related aspect, immunohistochemistry is performed, where the level of EMP2 expression is determined by antibody binding. In one aspect, the antibody binds to an amino acid sequence as set forth in SEQ ID NO: 1. In a further related aspect, determining the frequency of detecting EMP2 in a sample and comparing the frequency of detection with multiple variables to generate multivariate models for the identification of variables demonstrating statistical significance for patient survival is disclosed, where such variables include ER, PR, vascular, stage, diagnosis, disease status, and survival status.

In another embodiment, a method for monitoring the progression of endometrial premalignancy in a subject is disclosed including determining the level of endothelial membrane protein 2 (EMP2) polypeptide or polynucleotide in endometrial cells obtained at a first time, determining the level of EMP2 polypeptide or polynucleotide in endometrial cells obtained at a second time, and comparing the levels of EMP2 polypeptide or polynucleotide in the endometrial cells at the first and second times, where increased levels of EMP2 polypeptide or polynucleotide at the second time relative to the first time correlates with progression of endometrial premalignancy to a cancerous stage.

In one embodiment, a method of monitoring the stage of endometrial cancer in a subject is disclosed, including identifying a subject presenting endometrial cancer, determining epithelial membrane protein 2 (EMP2) polypeptide or polynucleotide level in a sample of endometrial tissue from the subject to establish, a baseline EMP2 level for the subject, measuring EMP2 polypeptide or polynucleotide level in an endometrial tissue sample obtained from the same subject at subsequent time points, and comparing the measured EMP2 polypeptide or polynucleotide level with the baseline EMP2 polypeptide or polynucleotide level, where an increase in measured EMP2 polypeptide or polynucleotide levels in the subject versus baseline EMP2 polypeptide or polynucleotide levels is associated with a cancer which is progressing, and where a decrease in measured EMP2 polypeptide or polynucleotide levels versus baseline EMP2 polypeptide or polynucleotide levels is associated with a cancer which is regressing or in remission.

In another embodiment, a method for screening a candidate compound that affects the endometrial premalignant phenotype is disclosed, including culturing endometrial tissue or cells, determining the level of endothelial membrane protein 2 (EMP2) polypeptide or polynucleotide in the cultured tissue or cells at a first time point, contacting the cultured tissue or cells with a candidate compound, determining the level of EMP2 polypeptide or polynucleotide into the cultured tissue or cells subsequent to compound contact, and comparing the levels of EMP2 before and after compound contact, where a change in the amount of binding after compound contact correlates with a compound induced alteration in the level of EMP2.

In a related aspect, an increase in the level of EMP2 correlates with the onset of or progression of an endometrial premalignant cell phenotype. In a further related aspect, a decrease in the level of EMP2 correlates with the regression of an endometrial premalignant phenotype.

In one aspect, the candidate compound is a modulator of a progesterone receptor DNA binding domain, NF-κB, a serum response element, or PPAR.

In one embodiment, a method for molecular analysis of endometrial samples is disclosed, including one or more endometrial samples, which samples include at least one control, exposing the one or more endometrial samples to different biological reagents that react with one or more biological markers, where at least one of the markers is epithelia membrane protein 2 (EMP2), performing one or more assays to detect one or more of the biological markers in the samples, and analyzing the assays to determine whether a reaction with a biological marker has occurred in the different samples, where an increase in the amount EMP2 in a sample relative to the control correlates with endometrial cancer (EC). In one aspect, images are obtained, where obtaining images comprises capturing digital images and storing the digital images. In another aspect, the one or more assays are selected from the group consisting of immunohistochemistry, PCR, or nucleic acid hybridization.

In a related aspect, the molecular analysis is an analysis of tissue, cellular, or subcellular distribution of the biological marker.

In a further related aspect, the method includes annotating information about the subjects and associating that information with the results of the image analysis, thereby obtaining correlations between the information and observed reactions.

In one embodiment, a method of treating endometrial cancer in a subject in need thereof is disclosed including administering a therapeutically effect amount of a pharmaceutical composition comprising a candidate compound identified by determining the level of endothelial membrane protein 2 (EMP2) expression in the cultured tissue or cells at a first time point, contacting the cultured tissue or cells with a candidate compound, determining the level of EMP2 expression into the cultured tissue or cells subsequent to compound contact, and comparing the levels of EMP2 before and after compound contact, where a change in the amount of binding after compound contact correlates with an agent induced alteration in the level of EMP2, and where the compound inhibits EMP2 expression, thereby modulating the regulation of GPI-lipid rafts and/or caveolae. In a related aspect, the modulation decreases surface expression of integrins and/or fibronectin.

In another aspect, the method further includes the administering of a ribozyme directed against EMP2 mRNA.

A method of treating endometrial cancer in a subject in need thereof comprising monitoring the level of EMP2 in combination with one or more therapeutic regimens.

In another embodiment, a kit is disclosed including an anti-epithelial membrane protein 2 (EMP2) antibody or antigen-binding fragment thereof, a container comprising an agent for determining the level of EMP2 in a sample, a control, and instructions to provide guidance for carrying out the assay embodied by the kit and for making a determination based upon that assay. In a related aspect, the antibody or antigen-binding fragment thereof is attached to a substrate, which substrate is applied to a sample from a patient or to a surface that may contain EMP2 and the surface of the substrate is then processed to assess whether specific binding occurs between the antibody and EMP2 or other component of the sample.

BRIEF DESCRIPTION OF THE FIGURES

FIG. 2B shows secretory endometrium. EMP2 staining (purple) is upregulated on the plasma membrane in secretory endometrium. Methyl green was used to stain nuclei. Magnification: 600×.

FIG. 14 illustrates how scFvs can be fused (e.g., by using SEQ ID NO:3) to intact Fc region containing C.sub.H1, C.sub.H2 and/or C.sub.H3 domains to produce intact chimeric antibody.

DETAILED DESCRIPTION OF THE INVENTION

Figure 1:
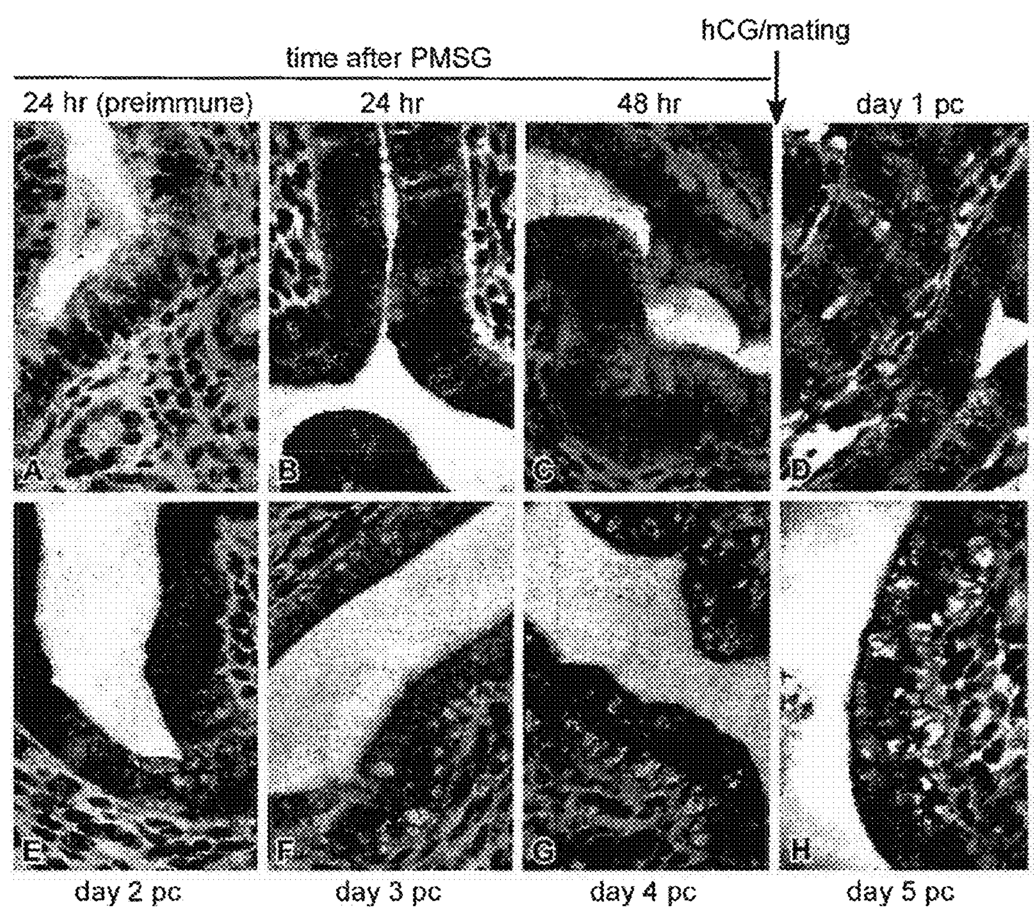
FIG. 1 shows immunostaining of mouse endometrium through the estrus cycle and mating. EMP2 expression was visualized using DAB; hemotoxylin was used to stain nuclei. Magnification, 600×.

Before the present composition, methods, and culturing methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms “a”, “an”, and “the” include plural references unless the context clearly dictates otherwise. Thus, for example, references to “the method” includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure. All publications mentioned herein are incorporated herein by reference in their entirety.

An “annotation”, refers to retrievably stored information that relates to the region of interest, the tissue sample, the tissue specimen, the tissue section, the tissue microarray, or the tissue block. For example, an annotation may be retrievably stored information regarding the source of a tissue sample; clinical, medical or demographic information about the donor of the tissue specimen; time, manner, location and/or institution in which the specimen was obtained; method of fixation, if any; type of tissue; histological or pathological features observable within the tissue, such as tumor type, tumor grade, acute and/or chronic inflammation, thromboses, or examples of normal (nondiseased) tissue or cells; information that enables location of histological or pathological features; tissue, cellular, or subcellular location and/or quantity of biological markers of interest; location information regarding one or more reference points or indicia in a tissue section, a tissue microarray section, or a tissue block; information regarding the distance of one or more reference points or indicia from a region of interest; information that enables location and/or retrieval of other tissue samples, tissue specimens, tissue sections, tissue microarrays, or tissue blocks, that may share one or more features in common with the tissue sample, section, microarray, etc. that is the subject of the annotation. The descriptions of the types of annotations that are possible are intended to be illustrative and not exhaustive. Virtually any type of information may the subject of en annotation. For example, an investigator may hypothesize that the development of a particular type of cancer, or a particular inflammatory or infectious disease, is related to an individual’s family history, astrological sign, birthplace, level of education, or exposure to a particular kind of animal. All such information could readily be stored as an annotation associated with the region of interest, tissue sample, tissue section, tissue microarray, or a tissue block. The annotation would then be available for review, and could serve as a tag for locating and/or retrieving tissue specimens, tissue microarrays, regions of interest, etc.

An “array” refers to a grouping or an arrangement, without necessarily being a regular arrangement.

“Antibody” refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and $F(ab)'_2$ fragments. The term “antibody”, as used herein, also includes antibody fragments either produced by the modification of whole antibodies or those synthesized de novo using recombinant DNA methodologies. It also includes polyclonal antibodies, monoclonal antibodies, chimeric antibodies, and humanized antibodies.

A “biological analysis” or “bioanalysis” is an analytical technique for obtaining biological information about a substrate, such as a tissue specimen. Particular examples of such techniques are the use of histological stains (such as H&E), immunohistochemical markers such as labeled antibodies for antigens of interest, and nucleic acid probes for detecting mRNA, DNA and other nucleic acids in the cells. Antibodies and other genetically engineered detection probes, antibody fragments, and reagents can be used. Nucleic acid probes could be used on proteins and antibodies to detect nucleic acid targets.

A “biological marker” is a biomolecule, a biochemical label, or other biological label that identifies a structure or function of interest in a biological specimen/sample.

“Biological assay” is a method of biological analysis, in which a biological substrate of interest is reacted with chemicals or biochemicals, where the reaction can be used to characterize the substrate (e.g., by function, presence or absence, etc.). Examples of biological assays are innumerable, and include DNA sequencing, restriction fragment length polymorphism determination, Southern blotting and other forms of DNA hybridization analysis, determination of single-strand conformational polymorphisms (Sakar et al., Nucleic Acid Res (1992) 20:871-8), comparative genomic hybridization (Kallioniemi et al., Science (1992) 258: 818-21), mobility-shift DNA binding assays, protein gel electrophoresis, Northern blotting and other forms of RNA hybridization analysis, protein purification, chromatography, immunoprecipitation, protein sequence determination. Western blotting (protein immunoblotting), ELISA and other forms of antibody-based protein detection, isolation of biomolecules for use as antigens to produce antibodies, PCR, RT PCR, differential display of mRNA by PCR (known in the art as differential display; Liang et al., Science (1992) 257:967-72), serial analysis of gene expression (U.S. Pat. No. 5,695,537), protein truncation test (Wimmer et al., Human Mutation (2000) 16(1):90-1; Moore et al., Molecular Biotechnology (2000) 14(2):89-97; Den Dunnen et al., Human Mutation (1999) 14(2):95-102). Protocols for carrying out these and other forms of cell free analysis are readily available to those skilled in the art, for example in Ausubel et al., Current Protocols in Molecular Biology, (c) 1998, John Wiley & Sons Ausubel et al., Short Protocols in Molecular Biology, (c) 1999, John Wiley & Sons; Maniatis et al., Molecular Cloning: A Laboratory Manual; and the series of publications known as Methods in Enzymology.

"Detecting" refers to determining the presence, absence, or amount of an analyte in a sample, and can include quantifying the amount of the analyte in a sample or per cell in a sample.

"Diagnostic" refers to identifying the presence or nature of a pathologic condition Diagnostic methods differ in their specificity and sensitivity. While a particular diagnostic method may not provide a definitive diagnosis of a condition, it suffices if the method provides a positive indication that aids in diagnosis.

"Nucleic acid sequence", "nucleotide sequence" and "polynucleotide sequence" as used herein refer to an oligonucleotide or polynucleotide, and fragments or portions thereof, and to DNA or RNA of genomic or synthetic origin which can be single- or double-stranded, and represent the sense or antisense strand.

A "ribozyme" is a molecule of RNA that has catalytic activity. The ribozymes of the invention are antisense oligonucleotides that bind and enzymatically cleave and inactivate EMP2 RNA. Useful ribozymes can comprise 5'- and 3'-terminal sequences complementary to the EMP2 RNA and can be engineered by one of skill on the basis of the EMP2 RNA sequence. Ribozymes of the invention include those having characteristics of group I intron ribozymes (Cech, 1995, Biotechnology 13:323) and others of hammerhead ribozymes (Edgington, 1992, Biotechnology 10:256).

Ribozymes of the invention include those having cleavage sites, such as GUA, GUU and GUC, Other optimum cleavage sites for ribozyme-mediated inhibition of telomerase activity in accordance with the present invention include those described in PCT Publications WO 94/02595 and WO 93/23569, both incorporated herein by reference. Short RNA oligonucleotides between 15 and 20 ribonucleotides in length corresponding to the region of the target EMP2 gene containing the cleavage site can be evaluated for secondary structural features that may render the oligonucleotide more desirable. The suitability of cleavage sites may also be evaluated, by testing accessibility to hybridization with complementary oligonucleotides using ribonuclease protection assays, or by testing for in vitro ribozyme activity in accordance with standard procedures known in the art.

As described by Hu et al., PCT Publication WO 94/03596, incorporated herein by reference, antisense and ribozyme functions can be combined in a single oligonucleotide. Moreover, ribozymes can comprise one or more modified nucleotides or modified linkages between nucleotides, as described above in conjunction with the description of illustrative antisense oligonucleotides of the invention.

As used herein, the terms "oligonucleotides" and "oligomers" refer to a nucleic acid sequence of at least about 10 nucleotides and as many as about 60 nucleotides, preferably about 15 to 30 nucleotides, and more preferably about 20-25 nucleotides, which can be used as a probe or amplimer.

An "antisense" oligonucleotide is a polynucleotide that is substantially or fully complementary to a target EMP2 polynucleotide and has the ability to specifically hybridize to the target EMP2 polynucleotide.

As used herein, the terms "complementary" or "complementarity" are used in reference to "polynucleotides" and "oligonucleotides" (which are interchangeable terms that refer to a sequence of nucleotides) related by base complementarity. Complementarity can be "partial" or "total". "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

The phrase "hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, 1993, "Overview of principles of hybridization and the strategy of nucleic acid assays," in Techniques in Biochemistry and Molecular Biology—Hybridization with Nucleic Probes. Generally, stringent conditions are selected to be about 5-10° C. lower than the thermal melting point ($T_m$) for the specific sequence at a defined ionic strength and pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as follows: 50% formamide, 5×SSC, and 1% SDS, incubating at 42° C., or, 5×SSC, 1% SDS, incubating at 65° C., with a wash in 0.2×SSC, and 0.1% SDS at 65° C.

"Amplification" is defined as the production of additional copies of a nucleic acid sequence and is generally carried out using polymerase chain reaction technologies well known in the art ("PCR Primer, a Laboratory Manual" (1995), Eds. C. W. Dieffenbach, and G. S. Dveksler, Cold Spring Harbor Press, Plainview N.Y.). As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

The term "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, messenger RNA (mRNA) is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe can be single-stranded or double-stranded. Probes are useful in the detection, identification and isolation of particular gene sequences. It is contemplated that any probe used in the present invention will be labeled with any "reporter molecule", so that it is detectable in any detection system, including, but not limited to enzyme, fluorescent, radioactive, and luminescent systems.

"Immunoassay" refers to a method of detecting an analyte in a sample involving contacting the sample with an antibody that specifically binds to the analyte and detecting binding between the antibody and the analyte. A variety of immunoassay formats can be used to select antibodies specifically immunoreactive with a particular protein. For example, solid-phase ELISA immunoassays are routinely used to select monoclonal antibodies specifically immunoreactive with a protein. See Harlow and Lane, in "Antibodies, A Laboratory Manual" (1988), Cold Spring Harbor Publications, New York, for a description of immunoassay formats and conditions that can be used to define specific immunoreactivity.

"Immunohistochemical" (abbreviated IHC) refers to specific binding agents, such as polyclonal and monoclonal antibodies, which recognize and mark antigens of interest, often by a chemical that shows that the agent has hound to the antigen of interest. An example of an IHC agent is EMP2 monoclonal antibody.

A "microarray" is an array that is miniaturized so as to require microscopic examination for visual evaluation.

Unless indicated otherwise by context, a "tissue specimen" refers to an intact piece of tissue, for example embedded in medium. A "tissue sample" refers to a sample taken from the specimen, or a sectioned portion of the sample. A sample can be either a tissue sample or a sample of other biological material, such as a liquid cellular suspension.

An observer can be a person viewing a slide with a microscope or an observer who views digital images acquired. Alternatively, an observer can be a computer-based image analysis system, which automatically observes, analyses, and quantitates biological arrayed samples with or without user interaction.

A "specific binding agent" is an agent that recognizes and binds substantially preferentially to a biological marker of interest, so that the agent provides potentially useful information about the biological marker. Examples of specific binding agents are polyclonal and monoclonal antibodies for an antigen of interest; proteins and proteins derivatives that interact or bind to other (for example, calmodulin or a labeled calmodulin derivative;), and nucleic acid probes such as DNA and RNA probes.

The term "tissue" as used herein includes cellular specimens unless the context clearly dictates otherwise. Such cellular specimens include, for example, cervical cell samples, vaginal washings, cell samples obtained by endoscopy, blood cells, bacteria, fungi, yeasts, and the like.

A "tumor" is a neoplasm that may be either malignant or non-malignant, "Tumors of the same tissue type" refers to primary tumors originating in a particular organ (such as endometrial, bladder, or lung). Tumors of the same tissue type may be divided into tumors of different sub-types (a classic example being bronchogenic carcinomas (lung tumors) which can be an adenocarcinoma, small cell, squamous cell, or large cell tumor).

The present invention relates to diagnostic assays, both quantitative and qualitative for detecting levels of EMP2 polypeptide or EMP2 nucleic acids in cells, tissues and bodily fluids, including determination of normal and abnormal levels. By "EMP2 polypeptide" is meant a protein or fragment thereof having an amino acid sequence identical to or substantially similar to that disclosed for EMP2 in WO 05/055808. Polypeptides which are "substantially similar" to the EMP2 protein disclosed in WO 05/055808 may contain conservative amino acid substitutions which do not alter the structure or activity of the EMP2 protein. By "EMP2 nucleic acids" is it meant to include both RNA and DNA encoding the EMP2 protein as disclosed in WO 05/055808 or a polypeptide with the same structure and activity. Thus, a diagnostic assay in accordance with the present invention for detecting over-expression of an EMP2 polypeptide compared to normal control bodily fluids or tissue samples via detection of elevated polypeptide or transcription levels may be used to detect the presence of cancers, including endometrial cancer.

Assay techniques that can be used to determine levels of a polypeptide or transcription levels of a gene, such as EMP2 of the present invention, in a sample derived from a host are well-known to those of skill in the art. Such assay methods include, but are not limited to, radioimmunoassays, reverse transcriptase PCR (RT-PCR) assays, gridding, immunohistochemistry assays, in situ hybridization assays, competitive-binding assays, Western Blot analyses and ELISA assays. Among these, ELISAs are frequently used to detect a gene's expressed protein in biological fluids. An ELISA assay initially comprises preparing an antibody, if not readily available from a commercial source, specific to EMP2, preferably a monoclonal antibody. In addition, a reporter antibody generally is prepared which binds specifically to EMP2. The reporter antibody is attached to a detectable reagent such as a radioactive, fluorescent or enzymatic reagent, for example horseradish peroxidase enzyme or alkaline phosphatase.

Nucleic acid methods can also be used to detect transcription levels of EMP2 as a marker for abnormal cell growth indicative of endometrial cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR(RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones arrayed on a grid can be used to both detect the expression of and quantitate the level of expression of that gene (gridding). It this approach, a cDNA encoding the EMP2 gene is fixed to a substrate. The substrate may be of any suitable type including but not limited to glass, nitrocellulose, nylon or plastic. DNA encoding the EMP2 clone is attached to the substrate and then incubated with the analyte, which may be RNA or a complementary DNA (cDNA) copy of the RNA, isolated from the tissue of interest. Hybridization between the substrate bound clone and the analyte can be detected and quantitated by several means including, but not limited to, radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

The above tests can be carried out on samples derived from patients' bodily fluids and tissue extracts (homogenates or solubilized tissue) such as from tissue biopsy and autopsy material. Levels of EMP2, determined in cells and tissues from a patient suspected of suffering from endometrial cancer by measuring the polypeptide or by transcription levels, are compared to levels of EMP2 in normal or control cells or tissues. Elevated levels of EMP2 measured in the patient as compared to levels in the same cells, tissues, or bodily fluids obtained from normal, healthy individuals are indicative of endometrial cancer. By "elevated levels" it is meant an increase in measured EMP2 levels in a patient as compared to EMP2 levels in the same normal cells or tissues. Detection of elevated EMP2 levels is useful in the diagnosis of endometrial cancer.

Further, monitoring of EMP2 levels in a patient diagnosed with endometrial cancer is useful in determining the onset of metastases in cancers which have not yet metastasized and in determining the stage of the cancer. For example, detection of EMP2 can be used in a method of monitoring endometrial cancer in a patient which has not metastasized for the onset of metastasis. In this method, a patient suffering from endometrial cancer that is not known to have metastasized is identified. EMP2 levels in a sample from the patient are then measured. These measured EMP2 levels are then compared with levels of EMP2 from a normal control sample. An increase in measured EMP2 levels in the patient versus the normal control is associated with a cancer which has metastasized.

The stage of endometrial cancer or uterine cancer in a patient suffering from endometrial cancer can also be determined. In this method a patient suffering from endometrial cancer is identified. EMP2 levels in a sample of tissue from the patient are measured to establish a baseline EMP2 level for said patient. EMP2 levels in samples of the same tissue are then determined at subsequent time periods such as scheduled check-ups with the patient's physician. Measured EMP2 levels are then compared with the baseline EMP2 levels for the patient. In this method, an increase in measured EMP122 levels in the patient versus baseline EMP2 levels in the patient is associated with a cancer which is progressing and a decrease in measured EMP2 levels versus baseline EMP2 levels is associated with a cancer which is regressing or in remission. Increases in measured EMP2 levels as compared to baseline EMP2 levels established for the patient may also be indicative of metastases.

In one embodiment, EMP2 immunohistochemistry functions as an "index diagnostic" to assign risk based on the presence of EMP2 expression. Therefore, based on this and other parameters (e.g., size of lesion), one can determine whether or not different therapeutic modalities (i.e., chemotherapy, radiation therapy, surgery) should be used. In a related aspect, methods for monitoring progression of endometrial premalignancy into a malignant phenotype is disclosed. For example, by using serial sampling (i.e., biopsy) of the endometrial tissue and observing the state of EMP2 expression in the lesions (e.g., individual endometrial glands), one can determine whether or not the endometrial premalignancies are progressing in a way that would indicate whether therapeutic intervention is advised or is successful.

One aspect of the invention is a method to determine the likelihood of a group of endometrial cells to become cancerous e.g., for these cells or glands to become premalignancies or progress to cancerous lesions. The endometrium is the uterine mucous membrane above the level of the internal os. The endometrium consists of a number of subsections such as the endometrial glands, epithelium lining of the endometrial surface, and the stroma (Novak's Gynecologic and Obstetric Pathology with Clinical and Endocrine Relations, E. R. Novak, and J. D. Woodruff, W B Saunders, Philadelphia, 1979. pp 171-172). The invention utilizes an agent, such as an antibody, that specifically binds to EMP2 protein to assess levels of EMP2 in endometrial tissue and cells. EMP2 expression in endometrial cells and tissue may also be assessed using nucleic acid analysis, such as selective amplification, or hybridization methods. A level of EMP2 above normal or control levels, indicates an increased likelihood that premalignant endometrial disease is present i.e., that the endometrial cells or tissues are premalignant.

According to the present invention, an agent that specifically binds to EMP2 is used in diagnosis of endometrial premalignancies. Preferably agents that bind EMP2 are EMP2 antibodies or antigen-binding fragments thereof, including polyclonal and monoclonal antibodies, prepared according to conventional methodology. Antibodies and antigen-binding fragments thereof that bind EMP2 are useful for determining EMP2 levels. Thus, terms such as "EMP2 antibody bound to the group of endometrial cells or glands" and "binding of the EMP2 antibody to the endometrial cell or gland" means the ability of the antibody to bind to and distinguish EMP2 from other proteins. As used herein, the term "antibody" is meant to include antibody or antigen-binding fragment thereof.

Antibodies and antigen-binding fragments thereof that bind EMP2 molecules and are useful for determining EMP2 levels, include but are not limited to: antibodies or antigen-binding fragments thereof that bind specifically to EMP2 and antibodies that bind specifically to fragments of EMP2.

Also useful in the invention are endometrial cell-associated molecules and the nucleic acids that encode them. Examples of endometrial cell-associated molecules are estrogen receptor polypeptides and progesterone receptor polypeptides. Endometrial cell markers are also useful in this invention and these are molecules that bind to the endometrial cell-associated molecules and include, but are not limited to: ligands such as estrogen and progesterone, and antibodies or antigen-binding fragments thereof that specifically bind to estrogen receptor polypeptides or progesterone receptor polypeptides.

Significantly, as is well-known in the art, only a small portion of an antibody molecule, the paratrope, is involved in the binding of the antibody to its epitope (see, in general, Clark, W. R. (1986) The Experimental Foundations of Modem Immunology, Wiley & Sons, Inc., New York; Roitt, L (1991) Essential Immunology, 7th Ed., Blackwell Scientific Publications, Oxford). The pFc' and Fe regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which, has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known, in the art, there are complementarity determining regions (CDRs), which directly interact with the epitope of the antigen, and framework regions (Frs), which maintain the tertiary structure of the paratope (see, in general, Clark, W. R. (1986) The Experimental Foundations of Modem Immunology, Wiley & Sons, Inc, New York; Roitt, I. (1991) Essential Immunology, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for $F(ab')_2$, Fab, Fv and Fd fragments; chimeric antibodies in which the Fc and/or FR, and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to EMP2 molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g., m13, fd, or lambda phage), displaying inserts from 4 to about 80 amino acid residues using conventional procedures. The inserts may represent, for example, a completely degenerate or biased array. One then can select phage-bearing inserts which bind to EMP2 molecules. This process can be repeated through several cycles of reselection of phage that bind to the EMP2 molecules. Repeated rounds lead to enrichment of phage bearing particular sequences. DNA sequence analysis can be conducted to identify the sequences of the expressed polypeptides. The minimal linear portion of the sequence that binds to the EMP2 molecules can be determined. One can repeat the procedure using a biased library containing inserts containing part of all of the minimal linear portion plus one or more additional degenerate residues upstream or downstream thereof. Yeast two-hybrid screening methods also may be used to identify polypeptides that hind to the EMP2 molecules. Thus, EMP2 molecules can be used to screen peptide libraries, including phage display libraries, to identify and select peptide binding partners of the EMP2 molecules.

As detailed herein, the foregoing antibodies and other binding molecules may be used for example to isolate and identify EMP2 protein. The antibodies may be coupled to specific diagnostic labeling agents for imaging of the protein or fragment thereof. The antibodies may also be used for immunoprecipitation, and immunoblotting EMP2 using standard methods known to those of ordinary skill in the art.

The immunohistochemistry assays described herein are carried out on samples (specimens) obtained from subjects. As used herein, a subject is a human, non-human primate, cow, horse, pig, sheep, goat, dog, cat, or rodent. In all embodiments, human subjects are preferred. As used herein, samples may be endometrial tissue or cells and may be obtained through standard methods such as biopsy, curettage or from body fluids such as menstrual fluid.

Particularly, important groups of subjects to which the present invention can be applied are premenopausal subjects, subjects suspected not to have endometrial cancer, subjects suspected of having endometrial cancer, and subjects with elevated unopposed estrogen levels. The term “unopposed estrogen” as used herein, means estrogen without progestin (Harrisons, Vol 14, Principles of Internal Medicine, Eds. Fauci, A. S., E. Braunwald, K. J. Isselbacher, J. D. Wilson, J. B. Martin, D. L. Kasper, S. L. Hauser, D. L. Longo, Tviti-Graw-Hill, N.Y., 1999). The term “elevated” as used herein, means levels of unopposed estrogen that exceed normal ranges, which are well known to one of ordinary skill in the medical arts. Elevated estrogen levels may arise from exogenous sources including, but not limited to, administration of estrogen without simultaneous progestin treatment. Elevated unopposed estrogen levels may also arise from endogenous sources such as polycystic ovarian disease.

The assay described herein involves measuring levels of EMP2 expression. Levels of EMP2 can be determined in a number of ways when carrying out the various methods of the invention. One measurement of the level of EMP2 is a measurement of absolute levels of EMP2. This could be expressed, for example, in terms of number of EMP2-positive cells per 100 cells in the tissue sample. Another measurement of the level of EMP2 is a measurement of the change in the level of EMP2 over time. Still another measurement relates to the number of endometrial glands that express EMP2 in a sample. These measurements may be expressed in an absolute amount or may be expressed in terms of a percentage increase or decrease over time. In one particularly important measurement, the level of EMP2 is measured in relation to levels in a control cell or gland sample.

Levels of EMP2 are advantageously compared to controls according invention. The control maybe a predetermined value, which can take a variety of forms. It can be a single cutoff value, such as a median or mean. It can be established based upon comparative groups, such as in groups not having elevated unopposed estrogen levels and groups having elevated unopposed estrogen levels. Another example of comparative groups would be groups having a particular disease, condition or symptoms and groups without the disease, condition or symptoms such as a group with endometrial premalignancy or endometrial cancer and a group without endometrial premalignancy or endometrial cancer. Another comparative group would be a group with a family history of a condition such as endometrial cancer and a group without such a family history. The predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk or highest amount of EMP2 and the highest quadrant or quintile being individuals with the highest risk or lowest amount of EMP2.

Still other controls can be based on other cells or glands within a single endometrial tissue sample. For example, endometrial glands that express EMP2 may be located adjacent to endometrial glands that express reduced levels of EMP2. These glands that express EMP2 can serve as positive controls for comparison with glands having reduced EMP2 antibody staining. Likewise, stromal and other cells in an endometrial tissue sample will express EMP2 and can be used as controls.

The predetermined value of a control will depend upon the particular population selected. For example, an apparently healthy population will have a different ‘normal’ range than will a population which is known to have a condition related to endometrial premalignancy, endometrial cancer, or elevated unopposed estrogen levels. Accordingly, the predetermined value selected may take into account the category in which an individual falls. Appropriate ranges and categories can be selected with no more than routine experimentation by those of ordinary skill in the art. By “elevated” it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include samples from control populations or control samples generated through manufacture to be tested in parallel with the experimental samples. As used herein a “matched” control means tissue or cells obtained at the same time from the same subject, for example, parts of a single biopsy, or parts of a single cell sample from the subject.

In a related aspect, the clinical populations can be analyzed by various statistical methods, including, but not limited to, multivariate analysis (see, e.g., Turner et al., J Clin Oncol (2001) 19(4):992-1000). Further, such analysis may include survival analysis and other techniques for elucidating clinical data (see, e.g., Klein and Moeschberger, Survival Analysis: Techniques for Censored and Truncated Data, 2003, Springer-Verlag Publishing Co., New York, N.Y.).

The various assays used to determine the levels of EMP2 include: specific binding assays, using materials which bind specifically to EMP2; gel electrophoresis; and the like. Immunoassays may be used according to the invention including sandwich-type assays, competitive binding assays, one-step direct tests and two-step tests such as described herein. Preferably EMP2 levels are determined by nondestructive imaging of EMP2 expression. In preferred embodiments, the imaging is real-time imaging and/or permits visualization of EMP2 distribution.

In the methods of the present invention, a labeling agent may be directly or indirectly bound to the EMP2-reactive monoclonal antibody in accordance with any known technique. When the labeling agent is directly bound, the labeling agent may desirably have introduced therein a functional group which is cable of binding to a EMP2-reactive monoclonal antibody. When the labeling agent is indirectly bound, bridging molecules such as avidin-biotin, for example, may be present between the labeling agent and the monoclonal antibody.

The labeling agent used in the process of the present invention may typically be an enzyme, a chemiluminescent reagent, a fluorescent reagent, and a radioisotope. Typical enzymes are horseradish peroxidase, alkaline phosphatase, β-galactosidase, luciferase, glucose-6-phosphate dehydrogenase (G6PDH), glucose dehydrogenase (GDH), and the like. Typical chemiluminescent reagents are luminol, isoluminol, an acridinium ester, a dioxethan, and the like. Typical fluorescent reagents are fluorescein isothiocyanate, umbelliferone, chelates of a rare earth metal, and the like. Typical isotopes are $^{125}$I, $^{14}$C and the like. Other labeling agents will be known to one of ordinary skill in the art.

When the labeling agent employed is an enzyme, a substrate is used for measuring the enzyme activity. The substrate employed is not limited so long as the substrate allows for the enzyme-substrate reaction to be measured as corresponding to the quantity of the enzyme present. For example, when the labeling agent is peroxidase, the substrate employed may be $H_2O_2$ and 3-3' diaminobenzidine (which results in the antibody binding site being stained brown) or $H_2O_2$ and 4-chloro-1-naphthol (resulting in a blue stain), tetramethylbendidine-$H_2O_2$, o-phenylenediamine-$H_2O_2$, 5-aminosalicylic acid-$H_2O_2$, and the like. When the labeling agent is alkaline phosphatase, the substrate employed may be, for example, toluidine salt of 5-bromo-4-chloro-3-indolylphosphate.

When the enzyme is β-galactosidase, the substrate employed may be, for example, p-nitrophenyl-β-D-galactopylanoside.

In some embodiments a qualitative determination with the naked eye of the quantity of the labeling agent in the specimen may be preferable. In such cases, a preferred measurement system is a colorimetric system wherein the labeled substance includes an enzyme such as peroxidase, alkaline phosphatase, or β-galactosidase as the labeling agent, and wherein an increase in quantity of the enzyme reaction product may be determined by means of a color development visible to the naked eye.

In addition to the immunohistochemical methods of the invention, selective amplification assays such as PCR, may be used to determine the expression levels of EMP2 and endometrial cell-associated molecules.

The specimen used in the process of the invention preferably is endometrial tissue or cells collected from the uterine cavity of a subject. The specimen collected from the uterine cavity may be used as collected. Ordinarily, however, the specimen will be treated with reagents appropriate for preparing the specimen for immunohistochemistry. The specimen may be collected by any usual clinical technique, such as biopsy. Another preferred sample or specimen in the process of the invention is cells or tissue collected from menstrual fluid. The cells may be used as collected or may be isolated from non-endometrial cells using standard cell separation procedures know to those of ordinary skill in the art.

The immunohistochemical assays used in the methods of the invention are standard and well known to one of ordinary skill in the art. Examples of such methods are provided below in the Examples. In general, the assay methods include some or all of the following steps. A specimen is prepared by collecting endometrial cells and/or endometrial tissue from the cavity of the uterus, and optionally treating the cells and/or the tissues in accordance with standard histochemical procedures. For example, the tissue sample may be fixed using formalin or other fixatives and further treated to optimize immunohistochemistry. In preferred embodiments, the tissue specimen is embedded in paraffin according to standard histological methods.

A predetermined amount of the specimen is then immobilized on a carrier, which can be, for example, a plastic or glass microscope slid; etc. The immobilized sample is then contacted with a EMP2-reactive antibody (preferably a monoclonal antibody), which optionally is labeled. The tissue sample can be stained using suitable histological counterstain for visualization of tissue (e.g., hematoxilim/eosin [H&E], methyl green) before or after the sample is contacted with the antibody. If the anti-EMP2 antibody is not labeled, it may be labeled subsequent to tissue binding by standard methods, such as by binding a labeled secondary antibody, or by contacting the antibody with a detectable reagent (such as an enzyme substrate, or an avidin-tagged detectable compound).

At various times during the methods, the immobilized sample can be washed to remove excess and/or non-specifically bound antibody, stain, detectable compounds, etc., as necessary. Wash solutions and methods for using them will be known to one of ordinary skill in the art.

The signal intensity of the labeled reagents bound to the tissue specimen is then measured as a determination of the level of EMP2 expression. The size of the endometrial glands or of other groups of cells in the tissue specimen can also be measured and the measurement used in the diagnostic methods of the invention as a further predictor of endometrial preamalignancies. The average size of the endometrial glands or of other groups of cells in the tissue specimen may be measured prior to treatment to establish a baseline size.

As disclosed herein, it is also possible to assess likelihood of endometrial premalignancy by monitoring changes in the absolute or relative amounts of EMP2 over time. For example, as disclosed herein, an increase in EMP2 expression in individual endometrial glands correlates with increasing likelihood of endometrial premalignancy arising in such glands. Accordingly one can monitor EMP2 expression over time to determine if the likelihood of endometrial premalignancy in a subject is changing. Increases in relative or absolute EMP2 may indicate an abnormality, for example an onset or progression of endometrial premalignancy or endometrial cancer. Decreases in amounts of EMP2 expressed in endometrial glands over time may indicate a decrease in premalignancy or endometrial cancer remission or regression.

The invention in another aspect provides a diagnostic method to determine the effectiveness of treatments. The "evaluation of treatment" as used herein, means the comparison of a subject's levels of EMP2 measured in samples collected from the subject at different sample times, preferably at least 1 month apart following treatment. The preferred time to obtain the second sample from the subject is at least one month after obtaining the first sample, which means the second sample is obtained at any time following the day of the first sample collection, preferably at least 30, 45, 60 or more days after the time of first sample collection.

The comparison of levels of EMP2 in two or more samples, taken on different days, allows evaluation of disease progression or regression and of the effectiveness of anticancer treatment. The comparison of a subject's levels of EMP2 measured in samples obtained on different days provides a measure to determine the effectiveness of any treatment to avoid or eliminate endometrial premalignancy.

As will be appreciated by those of ordinary skill in the art, the evaluation of the treatment also may be based upon an evaluation of the symptoms or clinical end-points of the associated disease. Thus, the methods of the invention also provide for determining the regression, progression, or onset of a condition which is characterized by increased levels of EMP2. In some instances, the subjects to which the methods of the invention are applied are already diagnosed as having a particular condition or disease. In other instances, the measurement will represent the diagnosis of the condition or disease. In some instances, the subjects will already be undergoing therapy for premalignancy or cancer, while in other instances the subjects will be without present therapy for premalignancy or cancer.

The diagnostic methods of the invention may also include a determination of the size of individual endometrial glands or groups of glands or cells in an endometrial tissue sample. The size of the glands or groups of cells can serve as a further diagnostic marker of endometrial premalignancies. Typically, progression to a cancerous phenotype includes an increase in cellular proliferation manifested as an increased size of a gland or group of cells. The size of a gland or group of cells can be measured by any convenient method, such as determining the maximum linear dimension of a gland or group of cells. The "maximum linear dimension" of a gland or group of cells is the longest straight linear measurement across the gland or group of cells. Sizes of glands or groups of cells which will confirm or contribute to a diagnosis of endometrial premalignancy can be absolute sizes or relative sizes as compared to control glands or groups of cells. For absolute sizes, a preferred maximum linear dimension of a gland or group of cells is at least one millimeter. More preferably, the maximum linear dimension is at least 2.0, 2.5, or 3.0 millimeters.

EMP2 levels in tissues and cells may also be assessed in tissue and cell culture. Such cultured cells and tissues may be from normal subjects or from subjects believed to have an endometrial premalignancy or endometrial cancer. The cultured cells and tissues may serve as a model for carcinogenesis in endometrial cancer and premalignancy and may also be used to screen candidate pharmacological agents for effects on the onset, progression or regression of endometrial premalignancy or endometrial cancer.

Standard methods of cell and tissue culture may be used to culture endometrial cells and tissues. Examples of such methods, although not intended to be limiting, include an explant model of short term culture of intact chunks of endometrial tissues (see: Bersinger et al., Early Pregnancy (1995) 1: 134-140; Dudley et al., Am J Obstet Gynecol (1992) 167:1774-1780) and the dissociation of stromal and epithelial parts and re-assembly as a co-culture (Arnold et al, Hum Reprod (2001) 16(5):836-845; Hopfer et al., Pathobiology (1994) 62(2):104-408. The invention includes the use of such culture systems for the diagnosis of endometrial premalignancy and endometrial cancer and for the screening of the effects of candidate pharmacological agents on the onset, progress, and regression of endometrial premalignancy or endometrial cancer.

In a related aspect, the promoter for EMP2 comprises binding element recognition sites for various DNA/nuclear binding factors, including progesterone receptor, NF-κB, serum response element, Peroxisome proliferators-activated receptor(PPAR)/retinoid X receptor (see, e.g., Table 1). As such, pharmacological candidates include, but are not limited to, antagonists and inhibitors of these DNA/nuclear binding factors. For example, for NF-κB, such candidates include, but are not limited to, a heterocyclic compound represented by formula (I) or a pharmaceutically acceptable salt thereof:

(I)

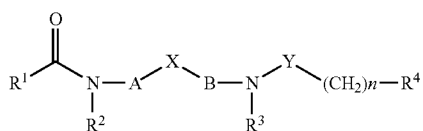

wherein $R^1$ is a cycloalkyl group, a cycloalkyl group having a substituent(s), wherein, when the cycloalkyl group is a cyclopropyl group said cyclopropyl group has a substituent(s), a cycloalkenyl group or a cycloalkenyl group having a substituent(s); each $R^2$ and $R^3$ is a hydrogen atom or an alkyl group; $R^4$ is an alkyl group, an alkyl group having a substituent(s), an alkenyl group, an alkenyl group having a substituent(s), a cycloalkyl group, a cycloalkyl group having a substituent(s), a cycloalkenyl group, a cycloalkenyl group having a substituent(s), an aryl group, an aryl group having a substituent(s), an aromatic heterocyclic group having at least one hetero-atom within a ring or an aromatic heterocyclic group having a substituent(s) and at least one hetero-atom within a ring; A is a heterocyclic ring or a heterocyclic ring having a substituent(s); B is an aromatic ring, an aromatic ring having a substituent(s), a heterocyclic ring or a heterocyclic ring having a substituent(s); n is an integer selected from 0 to 6; —Y— is an interatomic bond, —CO—, —CO—O—, —CO—$NR^5$—, —CS—$NR^6$, —SO—, —$SO_2$—, wherein each of $R^5$ and $R^6$ respectively is a hydrogen atom or an alkyl group; wherein —X— is an interatomic bond, —O—, —O—$CHR^7$—, —$CHR^8$—O—, —O—CO—, —CO—O—, —O—CS—, —CS—O—, —S—, —SO—, —$SO_2$—, —S—$CHR^9$—, —$CHR^{10}$—S—, —S—CO—, —CO—S—, —S—CS—, —CS—S—, —$SO_2$—$NR^{11}$—, —$NR^{12}$—$SO_2$—, —$NR^{14}$—$CHR^{15}$—, —$CHR^{16}$, —$NR^{17}$—, —CO—, —C(=$NOR^{18}$)—, —C(—$CHR^{19}$)—, —CO—$CHR^{20}$—, —$CHR^{21}$—CO—, —CO—$NR^{22}$—, —$NR^{23}$—CO—, —$CR^{24}$, $R^{25}$—, —$CHR^{26}$—$CHR^{27}$—, —$CR^{28}$, =$CR^{29}$—, —O—$CHR^{30}$—$CHR^{31}$—, wherein each of $R^7$, $R^8$, $R^9$, $R^{10}$, $R^{15}$, $R^{16}$, $R_{20}$, $R_{21}$, $R_{24}$, $R_{28}$, $R_{29}$, $R_{30}$ and $R^{31}$ respectively is either of a hydrogen atom or an alkyl group; each of $R^{11}$, $R^{12}$, $R^{13}$, $R^{14}$, $R^{17}$, $R^{18}$, $R^{19}$, $R^{22}$ and $R^{23}$ is either of a hydrogen atom, an alkyl group or an acyl group; each of $R^{26}$ and $R^{27}$ respectively is either of a hydrogen atom, a hydroxy group or an alkyl group; and $R^{25}$ is a hydrogen atom, a hydroxy group, an alkyl group, an alkyl group having a substituent(s), a hydrogen group, an alkoxy group, an alkylthio group, an acyloxy group, an amino group, an alkylamino group, an amino group substituted with an amino protective group, a carboxyl wow, an all group, an aminocarbonyl group, or a cyano group. See, e.g., U.S. Pat. No. 6,794,378.

In another aspect, for serum response element, such candidates include; but are not limited to, the agent

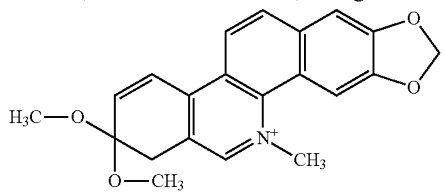

(i.e., Chelerythrine, see, e.g., U.S. Pat. No. 5,786,362).

In another aspect, for PPAR, such candidates include, but are not limited to, a PPAR antagonist of Formula (I) or (II), or pharmaceutically acceptable salts or solvates thereof, (I)

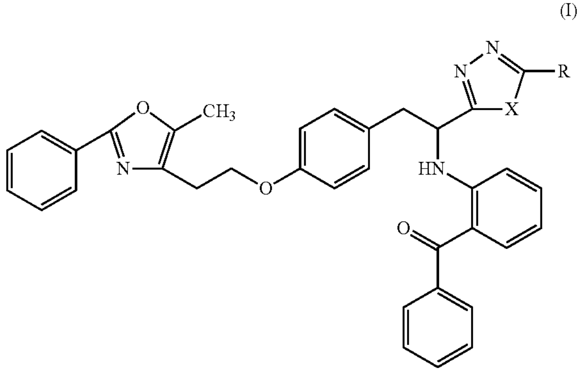

where in Formula (I) X is O, S, or NH;

and R is methyl, ethyl, n-propyl, cyclopropyl, ti-butyl, phenyl, or —$CH_2OCH_3$, (II)

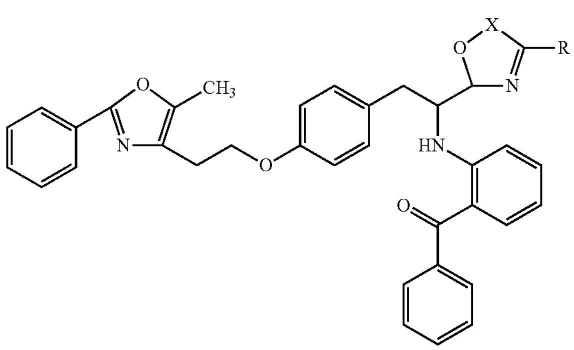

and where in Formula (II) X is C or N; and R is methyl, ethyl, n-propyl, i-propyl, —$CH_2OCH_3$, or —$CO_2CH_3$ (see, e.g., U.S. Pat. No. 6,506,781).

The invention also includes kits comprising the EMP2 binding agents described herein. The kit includes a package housing a container that contains an agent for determining the level of EMP2 in a sample. The kit may also include a control. The kit may also include instructions as described herein. The instructions typically will be in written form and will provide guidance for carrying out the assay embodied by the kit and for making a determination based upon that assay.

An example of a kit may include an antibody or antigen-binding fragment thereof that binds specifically to a EMP2 polypeptide, attached to a substrate (e.g. a dipstick). The substrate is then applied to a sample from a patient or to a surface that may contain EMP2 and the surface of the substrate is then processed to assess whether specific binding occurs between the antibody and a polypeptide or other component of the sample. As will be understood by one of skill in the art, such binding assay may also be performed with a sample or object contacted with an antibody or antigen-binding fragment thereof and/or EMP2 that is in solution, for example in a 96-well plate or applied directly to an object surface.

In one embodiment, endometrial tissue is examined by tissue micro arrays (TMA). For example, multiple tissue samples may be taken from multiple such tissue specimens, and the multiple samples from a particular specimen are similarly placed at corresponding positions in the multiple substrates. Each of the resulting substrates contains an array of tissue samples from multiple specimens, in which corresponding positions in each of the arrays represent tissue samples from the same tissue specimen. In particular examples, each substrate is then sectioned into multiple similar sections with samples from the same tissue specimen at corresponding positions of the sequential sections. The different sections may then be subjected to different reactions, such as exposure to different histological stains or molecular markers, so that the multiple "copies" of the tissue microarrays can be compared for the presence of reactants of interest. The large number of tissue samples, which are repeated in each of a potentially large number of sections of multiple substrates, can be exposed to as many different reactions as there are sections. For example, about 100,000 array sections may be obtained from a set of 1000 tissue specimens measuring 15×15×3 mm. This approach provides for high-throughput techniques, including rapid parallel analysis of many different tissue specimens.

In one embodiment, a sample can be processed by exposing different cut sections on the array to different biological reagents (such as standard stains, or immunohistochemical or genetic markers, oligonucleotides probes/primers, peptides, polypeptides, ligands, and small molecules, hormones, lipids, carbohydrates, lectins, etc.) that recognize biological structures in the cut sections. An imager then obtains an image of the cut processed sections, and an image processor identifies regions of the cut sections that contain images of biological interest (such as evidence of gene copy numbers), and stores images of the cut sections. If desired, quantities of biological reagents can be detected to quantify reactions (such as an amount of probe that hybridizes to the specimen as an indication of gene amplification or deletion), or to determine the distribution of the reagent in the sample.

The results of the image processing of any tissue microarrays can correlate the biological reactions of interest with identifying information about the cut sections and the subjects from whom the tissue specimens were obtained (such as clinical information about the subject). This information can be stored, for example, in a database that also includes the location of tissue donor specimens in the donor source, the location of recipient blocks in the recipient array, and the location of the tissue samples in the tissue microarray. Information in this sample database can be linked with information on the clinical, histological, and demographic information of the patients.

The disclosure also includes a method for performing molecular analysis of biological specimens by providing multiple sections each including multiple biological samples. In particular embodiments, subsets of the sections include multiple similar sections in which tissue samples from the same specimen are located at corresponding positions in different sections. The different sections are exposed to biological reagents (for example, different biological reagents) that react with biological substrates of interest in the biological samples, and images are obtained of the different sections after exposing the sections to the biological reagents. The images are then analyzed to determine whether a reaction with a substrate has occurred in the different sections, or specimen samples represented in the sections. The images also can be used to quantitate the degree of staining, analyze its homogeneity within and between tissue samples, as well as determine the subcellular distribution of the biomolecules of interest.

In particular embodiments, the different biological specimens are obtained from different specimens (such as tumors, timing tissue, or biopsy specimens), and in particular examples the different specimens are obtained from different subjects. Information about the biological specimens (such as clinical information about the subject) are correlated with the results of analyzing the images, to obtain relationships between the information and the reaction. For example, the stage of a tumor can be correlated with the presence of a particular biomarker, such as an immunohistochemical (IHC) marker, or gene amplification. The same gene of interest (such as EMP2) can be analyzed at both DNA, RNA and protein level from different samples (or the same sample, with multi-color detection methods) and the results of these molecular analyses correlated with one another. This method is capable of efficiently obtaining many data points, because multiple tests can relatively quickly be performed on multiple similar copies of samples from multiple specimens. For example, if samples from at least 10 different tissue specimens are present in each of at least 10 different sections, and the ten different sections are respectively exposed to 10 different reagents, then 100 data points can quickly be obtained.

In a particular embodiment of the method, the specimens are embedded in embedding medium to form tissue blocks, which are stored at identifiable locations in an array. The blocks are retrieved from the array, coordinates of particular areas in each of the tissue specimens in the blocks are determined, and tissue samples from the blocks are retrieved and inserted into receptacles of corresponding size in different tissue microarray blocks. After repeating this process with multiple blocks, to form a three-dimensional array of substantially parallel samples from a variety of different specimens, the tissue microarray blocks are then sectioned to make multiple similar tissue microarray sections that include samples of many different specimens. Each of these sections can then be subjected to treatment with multiple reagents, and subsequently analyzed for the presence of biological markers. This analysis can be performed by obtaining digital images of each section, or the samples in each specimen, and processing the image to identify specific regions of the section or sample that correspond to the presence of a biological marker, or to determine the amount and distribution of a biological marker that is present in the tissue microarray section. This information can be stored in a database for subsequent analysis and correlation with other information about the specimens and samples (such as clinical stage, or co-alteration of gene copies or expression).

In one embodiment of the method, a plurality of biological samples are provided at identifiable positions in the array, and the samples are subjected to a biological analysis. The biological analysis is usually performed after the samples are placed in the array, although the analysis can be performed prior to placement of the sample in the array. The array is then examined to detect a biological, histological or clinical marker, such as (a) the presence of a histologic sign of disease (e.g. cellular atypia or pyknotic nuclei) or (b) the presence of a molecular marker (such as an immunohistochemical marker or a nucleic acid probe) which is specifically bound to a substrate in the biological sample. The biological samples in the array may be samples of different tissue specimens (such as samples from many different tumors), or multiple samples from a single tissue specimen (for example to assess tissue homogeneity or heterogeneity). Alternatively, the biological samples in the array can include samples from different tissue specimens, as well as multiple samples from a single tissue specimen (for example, multiple copies of normal tissue as an internal control). This allows standardization of the molecular results from different sections of the same array or between multiple tissue microarray blocks that have different samples, but the same references included. The multiple substantial copies of the array can be subjected to the same biological analysis (such as immunohistochemical staining or molecular probing), or to different biological analyses, for example at a single location or at multiple different locations. The biological analysis may be performed, for example with a specific binding agent, such as an antibody or a nucleic acid probe, which substantially only or specifically recognizes and hinds to a biological substrate of interest.

In particular disclosed embodiments, the array may be a microarray, for example in which the plurality of biological samples includes at least 100, 500 or even 1000 or more biological samples placed at identifiable positions in the microarray. The identifiable positions may be coordinates of the array, such as coordinates of a substantially uniform matrix of rows and columns. Identifiers (such as electronic identifiers) can be associated with the array, and diagnoses may be associated with the identifiers. In this manner, a viewer may conveniently immediately determine an interpretation associated with a sample, for immediate confirmation of a correct interpretation or correction of an incorrect interpretation.

The array is particularly suitable for displaying tissue specimens, such as pathology specimens. In some examples, the pathology specimens are neoplastic tissue, non-neoplastic tissue, a combination of neoplastic and non-neoplastic tissue, and/or comparative specimens of different examples in a biological spectrum. For example, the comparative specimens may be different stages in development of a tumor, different types of tumor; and/or different stages in progression of a biologically dynamic tissue (such as uterine endometrial tissue at different days during a menstrual cycle). The samples may also include multiple different types of histological and biological regions of interest from a given tissue or tumor, defined by a user.

The use of such multiple specimens allows one to examine the variability in assaying a particular biomolecule from tissue sections, as well as to continue and minimize such variability. The biological interpretations of one or more dissemination copies may be combined to provide a composite reference copy interpretation (such as testing the variability of tumor grading or stain evaluation by different pathologists and averaging of the grades of a tumor as assigned by an expert panel of pathologists). The biological samples can also be used as a convenient holder for a library of multiple tissue samples, to replace space consuming libraries of slides on which tissue sections are mounted. Information about subjects from whom the samples were obtained can also be associated with each sample, and readily retrieved (for example electronically) so that clinical information (including clinical course) can be linked to the tissue.

The array technology allows a variety of different biological samples (for example samples from at least 10 different tissue specimens present in each different section) to be exposed to a variety of different biological analyses (for example at least 10 different reagents). Alternatively, the biological samples are obtained from at least 100 different tissue specimens, and are exposed to at least 100 different reagents. Images (such as digital images) of the arrays can be obtained, and the images analyzed, for example by quantifying the reaction with the substrate. The results of the biological analyses can be used for a variety of purposes, such as validating the presence of a particular biomarker in a set of tissues, determining the frequency and clinical associations of such a marker, evaluating a reagent for disease diagnosis or treatment; identifying a prognostic marker for cancer; assessing or selecting therapy for a subject; and/or finding a biochemical target for medical therapy. The biological sample may be a tissue specimen, as well as a hematological or cytological preparation of cells.

The phrase "pharmaceutically acceptable compositions" refers to molecular entities and compositions that are physiologically tolerable and do not typically produce an allergic or similar untoward reaction, such as gastric upset, dizziness and the like, when administered to a human. In one embodiment, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

In a related aspect, such pharmaceutical compositions may be administered to a subject as an ameliorative modality. As used herein, "ameliorative," means to improve or relieve a subject of symptoms associated with a disorder, and includes curing such a disorder.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

It will be apparent that any of the pharmaceutical compositions described herein can contain pharmaceutically acceptable salts. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In a related aspect, treatment regimens include surgical approaches such as extrafascial total abdominal hysterectomy with a wide vaginal cuff, combined with bilateral salpingo-oophrectomy and retroperitoneal lymph node sampling in the pelvic and para-aortic areas. Further, progesterone therapy, including continuous, large doses of nonestrogenic progesterone derivatives (e.g., hydroxyprogesterone caproate or medroxyprogesterone acetate or megestrol acetate are included. Moreover, cytotoxic chemotherapy in combination with the pharmaceutical compositions as disclosed include, for example, combinations of cyclophosphamide, doxortibicin, and cisplatin.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof; and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (loaned with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered, to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release (1998) 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol (1998) 16(7):307-21; Takakura, Nippon Rinsho (1998) 56(3):691-5; Chandran et al., Indian J Exp Blot (1997) 35(8):801-9; Margalit, Crit Rev Ther Drug Carrier Syst (1995) 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev India Pharm (1998) 24(12):1113-28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm (1998) 45(2):149-55; Zambaux et al., J Controlled Release (1998) 50(1-3):31-40; and U.S. Pat. No. 5,145,684.

All documents provided herein are incorporated by reference in their entirety.

The following examples are intended to illustrate but not limit the invention.

EXAMPLE 1

EMP2 is spatially and temporally regulated during the window of implantation in the endometrium.

EMP2, which is highly expressed in the uterus, translocates from an intracellular location to the apical surface of the endometrial epithelium during implantation in mice (FIG. 1).

EMP2 expression is regulated in part by steroid sex hormones.

Figure 2A:
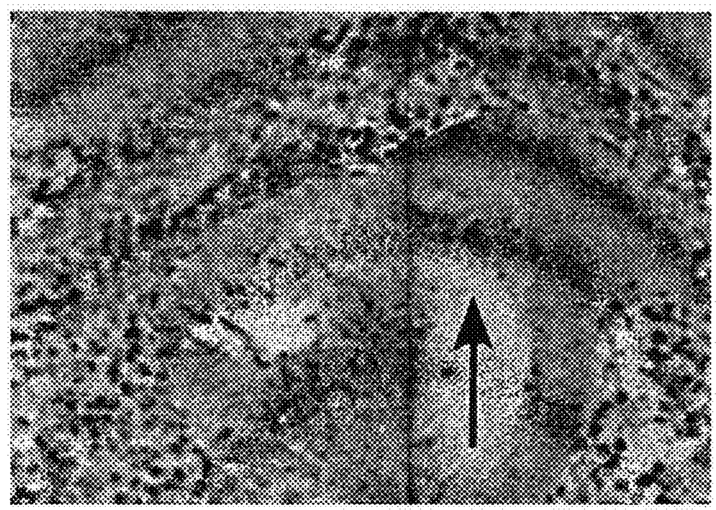
FIG. 2A shows proliferative endometrium. The arrow denotes the plasma membrane. Methyl green was used to stain nuclei. Magnification: 600×.
Figure 2B:
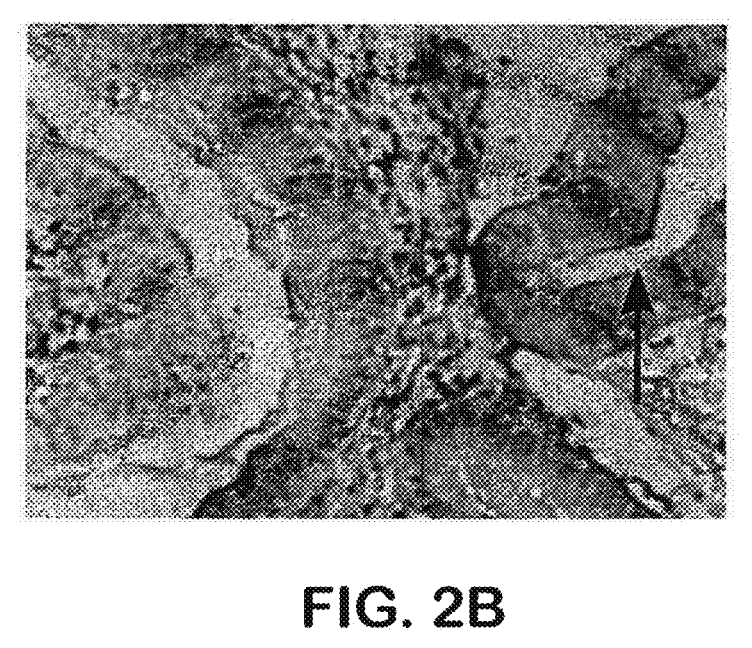

Normal endometrium is a dynamic organ, with a phenotype that alters with the menstrual cycle. Simply, this can be described as an interplay between estrogen during the proliferative phase and progesterone during the secretory phase (Mutter et al., Gynecol Oncol (2001) 83:177-185). First, FIG. 1 shows that EMP2 is temporally regulated in mice. Similarly in humans, EMP2 expression is upregulated in secretory endometrium compared to the proliferative phase (FIG. 2). This data suggests that EMP2 is in part regulated by progesterone. To support this conclusion, human and mouse promoters were analyzed using the Genomatrix MatInspector protocol. This analysis revealed four progesterone binding sites and 5 PPAR/RXR sites on both species (Table 1).

TABLE 1

SELECTED RESPONSE ELEMENTS LOCALIZED TO THE HUMAN EMP2 GENE

| Element | Number of Elements | Upstream locations (relative to translational initiation start sites |
|---|---|---|
| Progesterone Receptor Binding Site | 4 | 245-263, 470-488, 2071-2089, 2442-2460 |
| NF-κB | 4 | 42-56, 645-668, 924-938, 1207-1222 |
| Serum Response Element | 5 | 263-281, 965-983, 1230-1248, 1272-1290, 1329-1347 |
| PPAR/RXR heterodimers | 5 | 602-622, 852-872, 859-879, 1113-1133, 1643-1663 |

These observations support the notion that that the progesterone receptor, activated by the hormonal surge of progesterone, increase EMP2 expression and that inflammatory mediators, signaling through NE-κB pathways, impair endometrial EMP2 expression. Further, the regulatory elements as described offer targets for therapeutic manipulation of EMP2 expression. This is also supported by observations from PMP22, a close homologue of EMP2, whose promoter also harbors multiple progesterone receptor binding sites. Mutation of PMP22 disturbs expression of in peripheral myelin, resulting in the neuronal degenerative disease Charcot Marie Tooth Type I. Recently, progesterone was shown to restore normal PMP22 levels in these patients, and ameliorated the disease phenotype (Schumacher et al Brain Res Brain Res Rev (2001) 37:343-359). Though not to be bound by theory, pharmacological manipulation of EMP2 expression with progesterone, and possibly agonists or antagonists for the other regulatory element factors, should similarly provide therapeutic interventions to restore normal EMP2 expression, and thereby reverse aspects of the of the disordered phenotype and neoplastic progression in premalignant endometrium.

Aberrant EMP2 Expression in EC.

Figure 3:
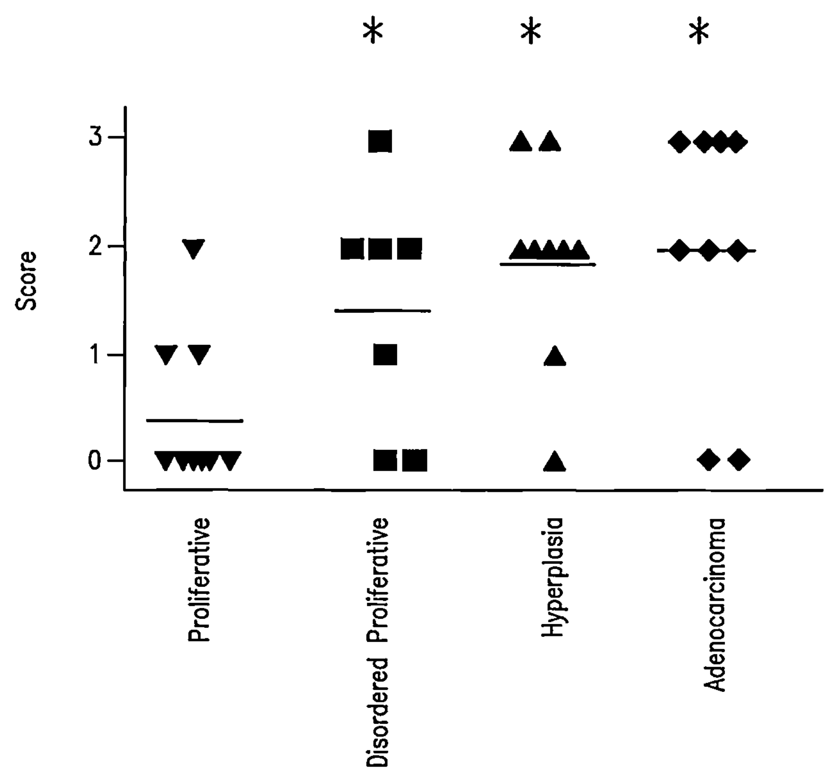
FIG. 3 graphically illustrates EMP2 expression level. EMP2 expression levels were scored from 0-3. Between 7-11 patients were analyzed in each group. EMP2 expression increases with premalignant potential. Mean: Proliferative Endometrium, 036; Disordered Proliferative, 1.43; Hyperplasia, 1.89; and Adenocarcinoma, 2.00. * denotes significant differences between means compared to normal tissue using the Student's T-test.

Sample were obtained from patients with disordered proliferative endometrium, hyperplasia, or endometrium carcinomas, and compared to normal proliferative endometrium. Atypical hyperplasia and simple hyperplasia were grouped together. EMP2 expression levels were scored from 0-3, 3 being the highest expression. Immunochemical analysis of EMP2 expression levels correlated with increasing premalignant potential (Means, Normal Proliferative 0.36; Disordered Proliferative 1.43; Hyperplasia 1.89), and is highest in patients with EC (mean 2.0; FIG. 3).

EMP2 Traffics Select Proteins Onto the Plasma Membrane.

EMP2 reciprocally regulates the GPI-associated and caveolin-associated caveolae GEM compartments. At least two distinct lipid rafts exist within cells: GPI-anchored protein and caveolae (Abrami et al., J Biol Chem (1999) 274:3910-3917; Nichols et al., J Cell Biol (2001) 153:529-541). It has been suggested that cells utilize distinct rafts to permit regulation of distinct biological processes (Leitinger and Hogg, J Cell Sci (2002) 115:963-972; Moffett et al., J Biol Chem (2000) 275:2191-2198; Melkonian et al., J Biol Chem (1999) 274:3910-3917).

Figure 4:
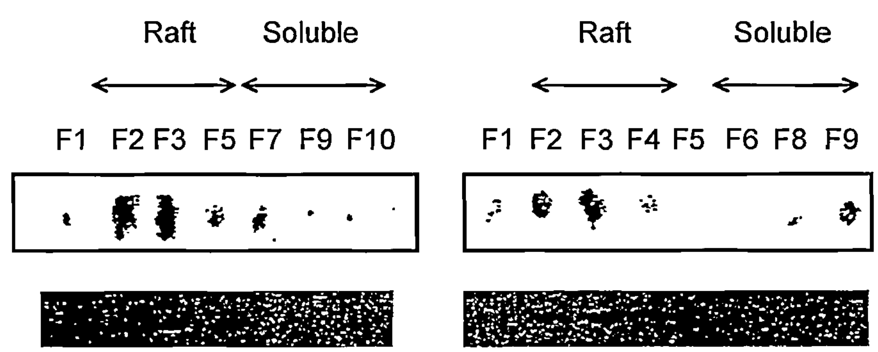
FIG. 4 shows that EMP2 colocalizes with the GEM marker cholera, toxin (CHTX) in (A) HEC1A and (B) RL95-2 cells in the presence of 1% Brij.

Using sucrose gradient fractionation, EMP2 was observed to associate with GEMS in a variety of cell types including B-cells. NIH3T3 fibroblasts, and human endometrial carcinoma cell lines RL95-2 and HEC1A (FIG. 4) (See also, Wadehra et al., Clin Immunol (2003) 107:129436; Wadehra et al., Mol Biol Cell (2004) 15:2073-2083 for method, incorporated herein by reference).

In NIH3T3, B-cells, and endometrial carcinoma cell lines, EMP2 levels strikingly increased the surface expression of GPI-anchored proteins (detected by aerolysin immunofluorescence), select integrins, and MHC class I molecules. In contrast, EMP2 negatively regulated caveolin-1, both at the protein and steady state RNA levels. Thus, in a variety of cells, EMP2 affects trafficking of proteins in two ways: positive regulation of GPI-lipid rails and negative regulation of caveolae.

Integrins are Dysregulated in EC.

Integrins are ubiquitous cell adhesion molecules that are involved in maintaining normal tissue morphology and have been implicated in the aggressive behavior of several malignancies. Studies have shown that β1C expression, for example, increases in EC compared with normal proliferative endometria at both the protein and mRNA level (Lovecehio et al., Am J Pathol (2003) 163:2543-2553).

Figure 5:
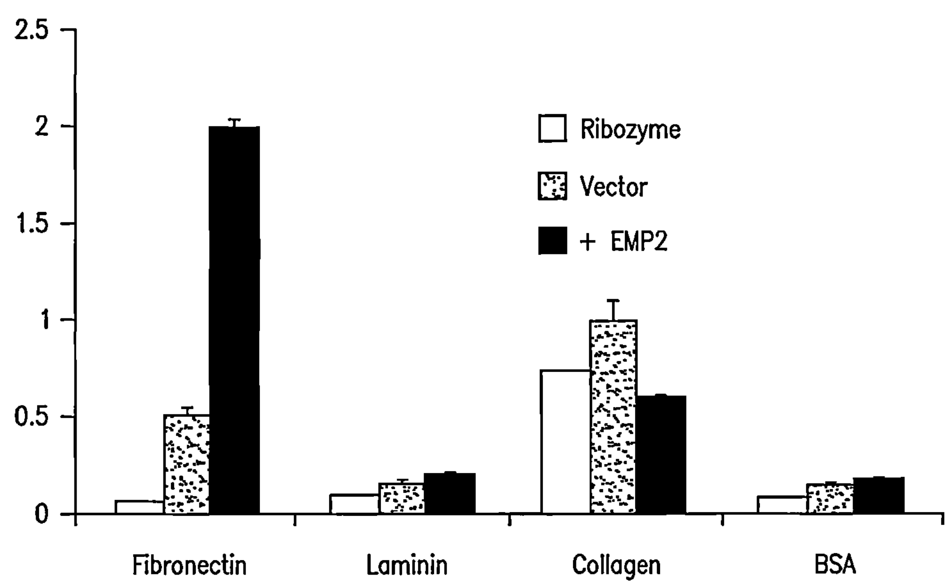
FIG. 5 illustrates graphically that EMP2 expression selectively augments laminin binding. HEC1A stable transformants (vector, EMP2, and EMP2 ribozyme) were incubated in wells with indicated proteins (serum free), and assayed for adherence. Mean+/−SD for triplicate wells.

In EC cell lines, EMP2 interacts with and regulates expression of certain integrin isoforms. The endometrial carcinoma cell line HEC1A was assessed where EMP2 expression was up (ectopic overexpression) or down modulated (ribozyme cleavage). Analysis of these cell lines revealed a regulatory role of EMP2 on integrin is isoform expression. Ectopic EMP2 expression selectively increased integrin avβ and augmented fibronectin binding (FIG. 5).

Comprehensive Tissue Microairay (TMA).

UCLA Medical Center patients (Westwood and Santa Monica), age 35 to 61 years, were ascertained with initial diagnosis of an EC malignant state (disordered proliferative, simple, and complex hyperplasia), or EC itself, by electronic search of the Tamtron Pathology database (1955-present). Patients with available follow-up were identified by a DIA electronic medical search methodology. The DIA. (data, information, analysis) methodology identifies events of care for index patients in Tamtron, Meditech (Clinical Lab database), and PLMS (combined medical center database for financial, demographic, and clinical diagnostic coding). Entry criteria were index patients with 10 year follow-up (premalignant and EC groups), progression to EC (premalignant group), or death (EC group). One hundred and twenty (120) entrants for each were sought for disordered proliferative disease, simple/complex hyperplasia, and EC. In addition, 30 cases each of control patients were identified (age 35-61 years) with normal or secretory endometrial biopsies.

In collaboration with the JCCC tissue microarray core, replicate 280 member microarrays were designed, bearing 80 specimens each of atypical proliferation, simple+complex hyperplasia, and EC. The microarray also included 20 cases each of normal proliferative and secretory endometrium. Specimens from patients meeting study follow-up criteria were selected from the UCLA Hospitals paraffin tissue archive using a DIA electronic medical record search methodology. Annotation was completed and validated by a combination of DIA methodology and manual chart review. Among the data elements were tumor grade and stage at each surgical event, treatment, disease-free interval, and disease status at death. The grades and stages of the patients with EC was determined in accordance with the criteria of the International Federation of Gynecology and Obstetrics (FIGO) (See Table 2).

TABLE 2

STAGING OF ENDOMETRIAL CARCINOMA AS A GUIDE TO TREATMENT AND PROGNOSIS

| Stage | Definition |
|---|---|
| IA (G1, 2, 3)† | Tumor limited to endometrium |
| IB (G1, 2, 3) | Invasion to <½ myometrium |
| IC (G1, 2, 3) | Invasion to >½ myometrium |
| IIA (G1, 2, 3) | Tumor involves only endocervical glands |
| IIB (G1, 2, 3) | Invasion to cervical stroma |
| IIIA (G1, 2, 3) | Tumor has invaded serosa and/or adnexa and/or peritoneal cytologic results are positive |
| IIIB (G1, 2, 3) | Metastases to the vagina |
| IIIC (G1, 2, 3) | Metastases to pelvic and/or para-aortic lymph nodes |
| IVA (G1, 2, 3) | Tumor has invaded bladder and/or bowel mucosa |
| IVB | Distant metastases, including intra-abdominal and/or inguinal lymph nodes |

†G1 = ≤5% of a nonsquamous or nonmorular solid growth pattern; G2 = 6-50% of a nonsquamous or nonmorular solid growth pattern; G3 = 50% of a nonsquamous or nonmorular solid growth pattern. Notable nuclear atypia, inappropriate for the architectural grade, raises the grade of a grade 1 or 2 tumor by 1. In serous adenocarcinomas, clear cell adenocarcinomas, and squamous cell carcinomas, nuclear grading takes precedence. Adenocarcinoma with squamous differentiation are graded according to the nuclear grade of the glandular component.

Immunohistochemistry was performed on the TMA to assess EMP2 expression in the presentation and follow-up specimens, and levels of expression were quantitated via two methods. For premalignant progression, data from the premalignant case set were analyzed by quantitative statistical comparison of EMP2 levels by automated image analysis. Two experts then determine the subcellular distribution of EMP2, and correlate it with three outcomes categories (return to normal; persistent premalignant condition; and EC). For EC progress, data from the EC case set was quantitatively compared by automated image analysis with respect to presenting grade/stage, and up to 10 year outcome (survival and disease free survival).

The subcellular distribution of EMP2 was quantitatively characterized using a digital imaging and an image analysis protocol. EMP2 results were obtained for 103 endometrial carcinomas (EC), prepared as a paraffin-block tissue microarray (collaboration with Dr. Robert Soslow, Memorial Sloan-Kettering Cancer Center). Of the 103 endometrial carcinomas, clinical information was available for 99 patients (Table 3). The median follow-up for alive patients was 34 months (range 1-240 months).

TABLE 3

CLINICAL CHARACTERISTICS OF PATIENTS

| | | Frequency (5) | | |
|---|---|---|---|---|
| Variable | | EMP2 (−) | EMP2 (+) | p-value |
| | Mean Age | 65 | 65 | 0.86 |
| ER | (−) | 63 (89%) | 10 (83%) | 0.31 |
| | (+) | 28 (31%) | 2 (17%) | |
| PR | (−) | 61 (67%) | 9 (75%) | 0.58 |
| | (+) | 30 (33%) | 3 (25%) | |
| Vascular | N | 55 (63%) | 6 (50%) | 0.37 |
| | Y | 32 (37%) | 6 (50%) | |
| Stage | IA | 9 (10%) | 0 (0%) | 0.13 |
| | IB-IIB | 51 (59%) | 5 (42%) | |
| | IIIA-IV | 27 (31%) | 7 (58%) | |
| Diagnosis | Clear Cell | 3 (3%) | 0 (0%) | |
| | Endometrioid | 65 (75%) | 9 (75%) | 0.92 |
| | Serous | 7 (8%) | 1 (8%) | |
| | Other | 12 (14%) | 0 (0%) | |

TABLE 3-continued

CLINICAL CHARACTERISTICS OF PATIENTS

| Variable | | Frequency (5) EMP2 (−) | EMP2 (+) | p-value |
|---|---|---|---|---|
| Disease Status | No Disease | 58 (71%) | 3 (25%) | 0.005 |
| | Disease | 29 (29%) | 9 (75%) | |
| Survival Status | NED | 54 (62%) | 3 (25%) | |
| | AWD | 8 (9%) | 2 (17%) | 0.05 |
| | DOD | 21 (24%) | 7 (58%) | |
| | DOC | 4 (5%) | 0 (0%) | |

EMP2 expression was assessed using immunohistochemistry with antisera produced in rabbits to extracellular peptide (EDIHDKNAKFYPVTREGSYG, SEQ ID NO: 1) of the human EMP2 protein. Negative control for each sample was stained with preimmune sera. TMA sections were deparaffinized with xylene and rehydrated with a graded alcohol series. Endogenous peroxidases were blocked and samples placed in citrate buffer (10 mmol/L, pH 6) and heated in a steamer for 15 mins. Sections were then blocked in 10% normal goat serum, and incubated with the primary EMP2 antisera for 50 min at RT. The anitsera was used as the purified IgG fraction, and was a high titer reagent (effective at ~1 μg/sample) with proper specificity, although other purified fractions will work (e.g., IgM). Sections were then incubated for 15 mins with the Vectastain biotin-secondary antibody, followed by the streptavidin-tertiary antibody. Sections were developed using Vector DAB, and nuclei were counterstained using hematoxylin.

Figure 6:
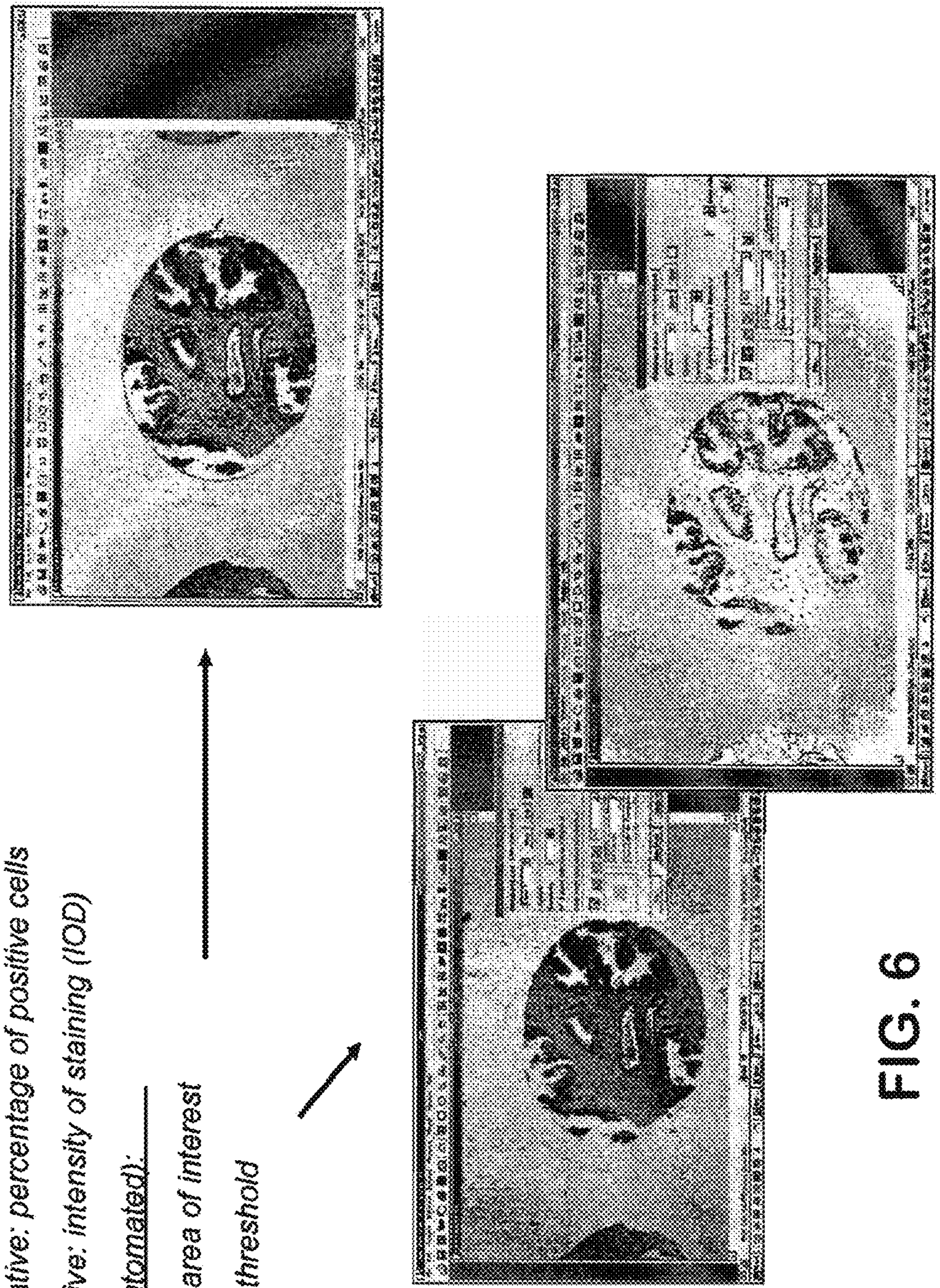
FIG. 6 shows screen shots from an Image Pro-Plus® system.
Figure 7:
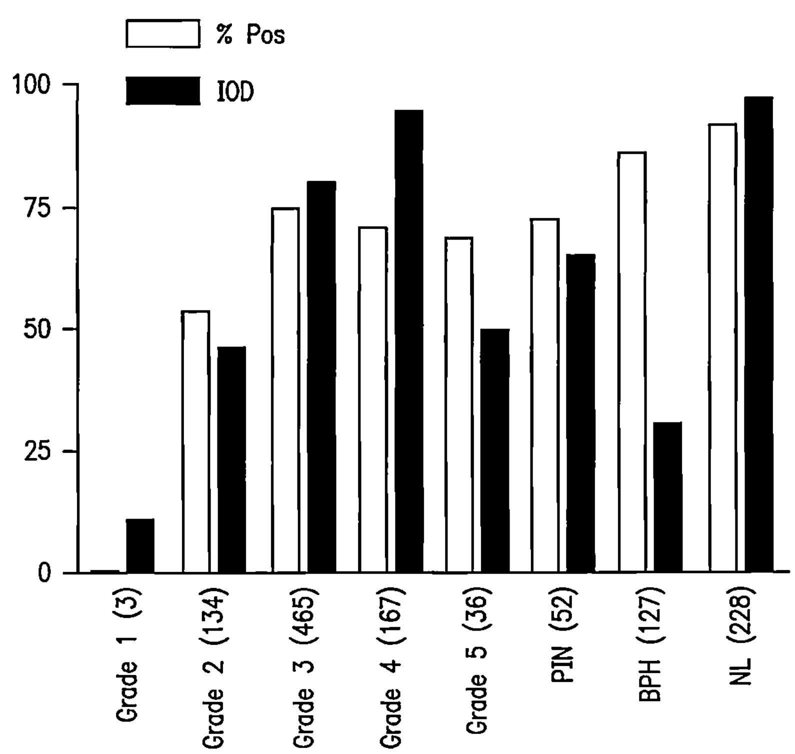
FIG. 7 shows an example of automated image analysis. Data is from a tissue microarray experiment of p27 staining in prostate cancer. Computerized scope represents the percentage of cells positive (white bar) with intensity of the stain (black bar). PIN, prostate intraepithelial neoplasia; BPH, benign prostatic hyperplasia; nl, normal.
Figure 8:
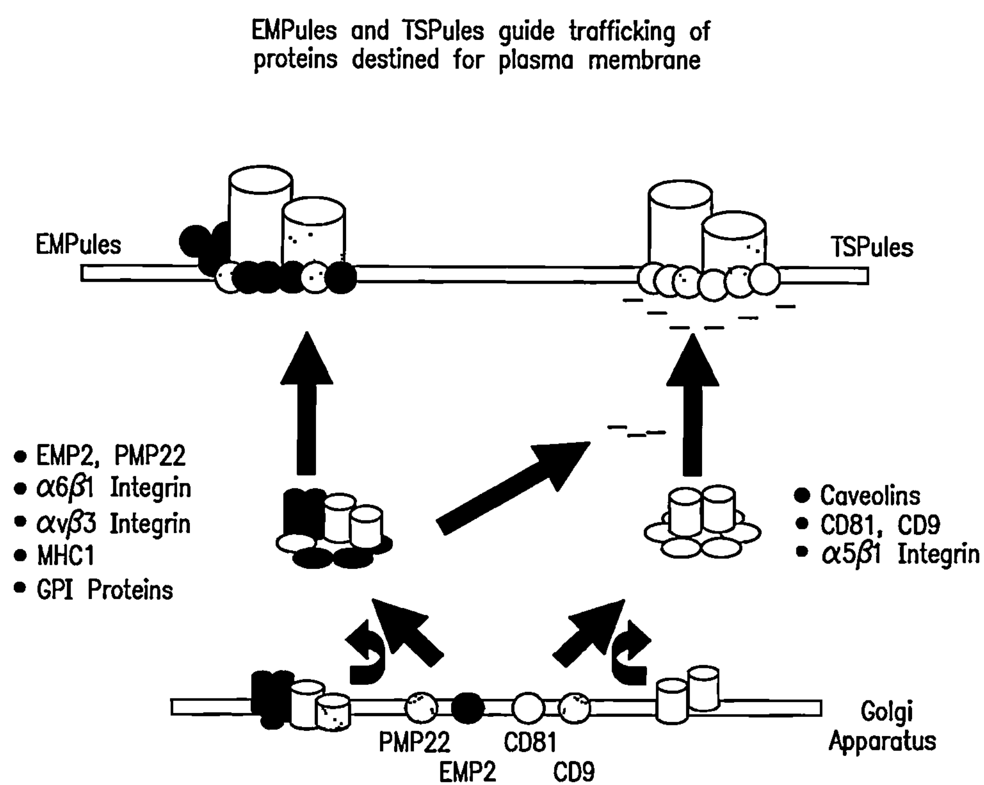
FIG. 8 illustrates Empties and TSPules as they guide trafficking of proteins destined for the plasma membrane.
Figure 9:
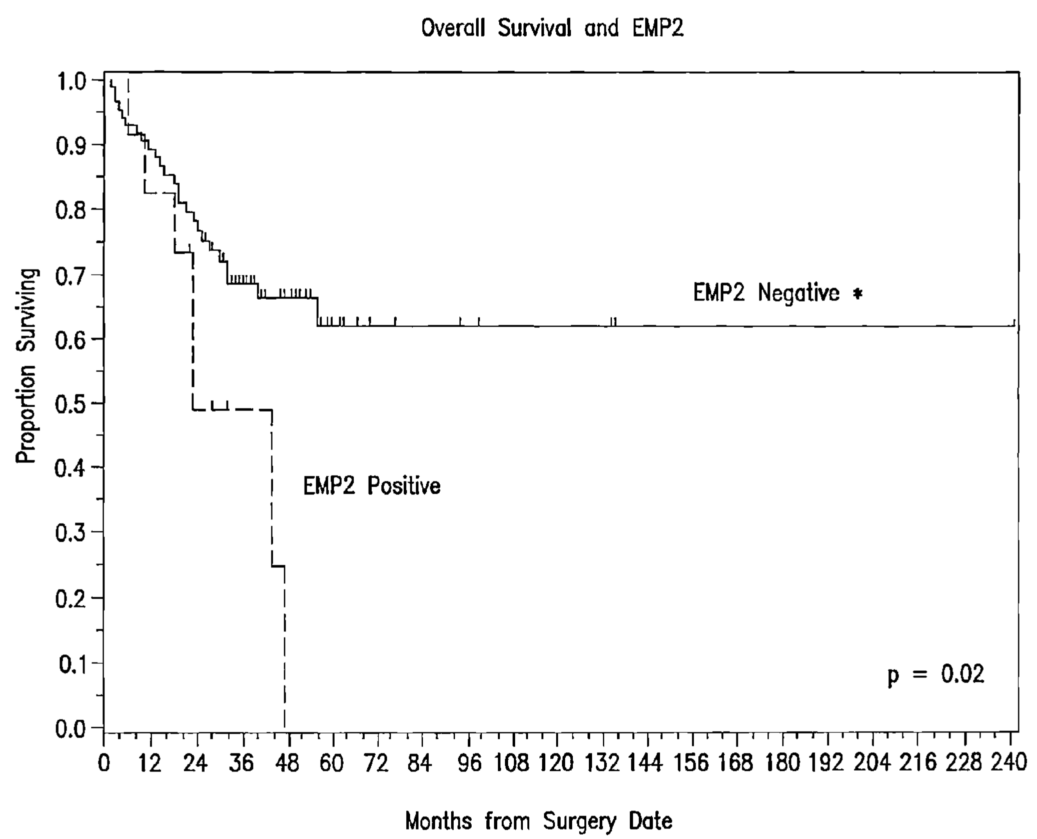
FIG. 9 graphically illustrates the correlation between overall survival and EMP2 expression.
Figure 10:
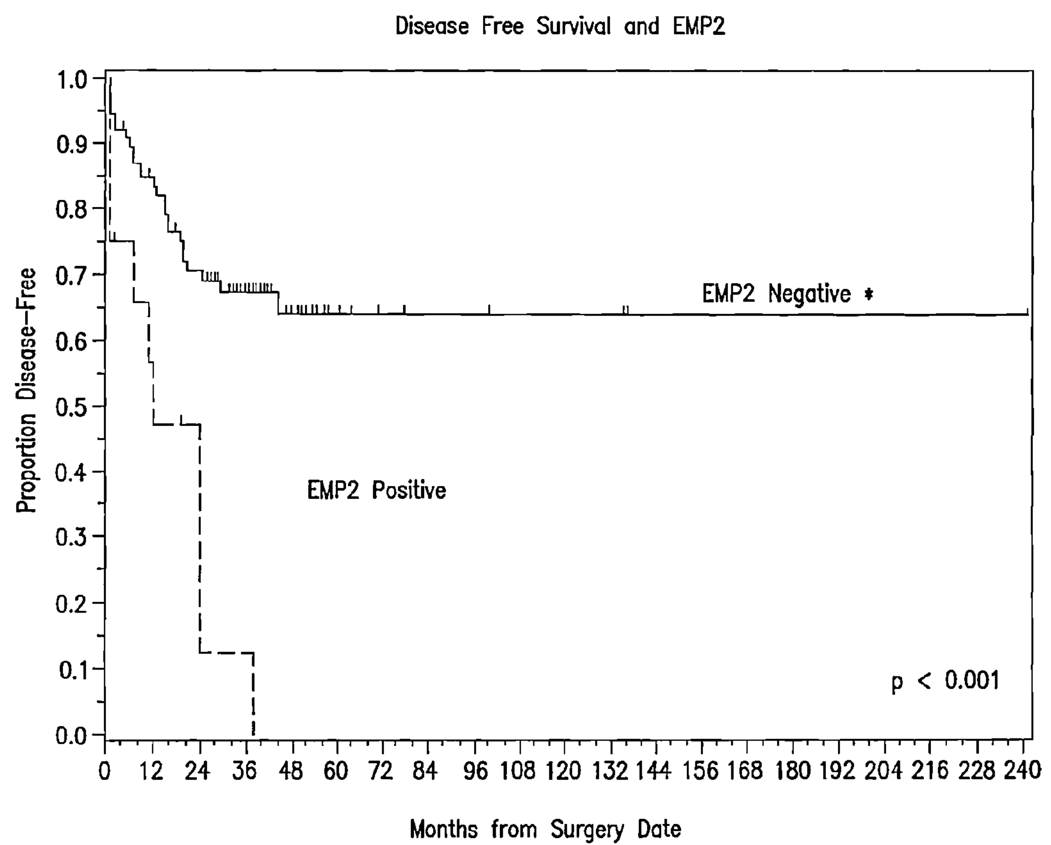
FIG. 10 graphically illustrates the correlation between disease free survival and EMP2 expression.

Automated image analysis was used as a method to assess EMP2 expression in tissues. The digital imaging system (e.g., Olympus DP11) coupled with the Image Pro-Plus system from Media Cybernetics (Silver Spring, Md.), was used for hardware and software. The validated systems was designed to provide fast and accurate image analysis with a full range of counting, sizing, and image enhancement tools. The image is quantitated through digitization with the pixel depth or bits-per-pixel (BPP) assigned in gray scale. Images are further enhanced by gamma correction, a specialized form of contrast enhancement (FIG. 6). Histogram analysis provides data which is instantly imported into an Excel spreadsheet for tabulation and quantitation (FIG. 7). The data was extremely reproducible with greater than 99.9% session to session accuracy. Chi-squared tests were used to determine statistical significance for association for categorical variables and t-tests for continuous variables. Survival estimates were generated using Kaplan-Meier methods. Univariate p-values comparing survival curves (FIGS. 9 and 10) were calculated using the log-rank statistic (Tables 4 and 5).

TABLE 4

UNIVARIATE ANALYSIS OF OVERALL SURVIVAL

| Variable | N | % Alive | Median Overall Survival (95% CI) | 2 Year Overall Survival Rate (95% CI) | Hazard Ratio (95% CI) | p-value (log-rank) |
|---|---|---|---|---|---|---|
| Age | | | | | | |
| <65 | 48 | 79% | NR‡ | 79% (67-91%) | 1.00 | 0.02 |
| ≥65 | 51 | 57% | 3.3 (2.3-NR) | 71% (67-84%) | 2.3 (1.1-5.0) | |
| ER | | | | | | |
| (−) | 71 | 61% | 4.7 (2.5-NR) | 68% (56-78%) | 1.00 | 0.02 |
| (+) | 28 | 86% | NR (3.9-NR) | 98% (89-100%) | 0.31 (0.11-0.88) | |
| PR | | | | | | |
| (−) | 89 | 56% | 3.7 (2.3-NR) | 65% (63-78%) | 1.00 | 0.002 |
| (+) | 30 | 90% | NR | 97% (90-100%) | 0.19 (0.06-0.63) | |
| Vascular | | | | | | |
| N | 81 | 84% | NR (2.3-NR) | 89% (80-97%) | 1.00 | <0.001 |
| Y | 36 | 42% | 2.1 (1.6-3.9) | 53% (35-70%) | 4.8 (2.3-10.2) | |
| Stage | | | | | | |
| IA | 9 | 100% | NR | 100% (NE*) | 1.00 | 0.003 |
| IB-IIB | 56 | 73% | NR (4.7-NR) | 81% (70-92%) | NE | |
| IIIA-IV | 34 | 50% | 2.7 (1.1-NR) | 59% (41-76%) | NE | |
| Diagnosis | | | | | | |
| Clear Cell | 3 | 67% | NR (2.3-NR) | 100% (NE) | 1.00 | |
| Endometrioid | 74 | 73% | NR (4.7-NR) | 82% (73-91%) | 1.2 (0.18-6.9) | <0.001 |
| Serous | 8 | 86% | NR (3.9-NR) | 100% | 0.81 (0.05-13) | |
| Other | 14 | 29% | 1.3 (0.5-1.9) | 17% (0-36%) | 8.0 (0.96-65) | |
| EMP2 | | | | | | |
| (−) | 87 | 71% | NR (4.7-NR) | 76% (69-87%) | 1.0 | 0.04 |
| (+) | 12 | 42% | 1.9 (1.5-3.9) | 49% (16-82%) | 2.4 (1.0-5.6) | |

‡NR: Not reached

*NE: Not Estimable

TABLE 5

| UNIVARIATE ANALYSIS OF DISEASE-FREE SURVIVAL | | | | | | |
|---|---|---|---|---|---|---|
| Variable | N | % Disease-Free | Median Disease-Free Survival (95% CI) | 2 Year Disease-Free Survival Rate (95% CI) | Hazard Ratio (95% CI) | p-value (log-rank) |
| Age | | | | | | |
| <65 | 46 | 72% | NR‡ (3.7-NR) | 78% (65-91%) | 1.0 | 0.04 |
| ≥65 | 49 | 53% | 1.9 (1.3-NR) | 48% (32-53%) | 2.0 (1.0-4.0) | |
| ER | | | | | | |
| (−) | 67 | 55% | 3.7 (1.6-NR) | 56% (43-68%) | 1.0 | 0.04 |
| (+) | 28 | 79% | NR | 79% (63-96%) | 0.41 (0.17-0.99) | |
| PR | | | | | | |
| (−) | 65 | 54% | 3.1 (1.3-NR) | 52% (39-65%) | 1.0 | 0.01 |
| (+) | 30 | 80% | NR | 85% (71-99%) | 0.34 (0.14-0.81) | |
| Vascular | | | | | | |
| N | 60 | 75% | NR | 77% (65-89%) | 1.0 | <0.001 |
| Y | 35 | 40% | 1.5 (0.5-NR) | 38% (20-55%) | 3.5 (1.8-8.9) | |
| Stage | | | | | | |
| IA | 9 | 100% | NR | 100% (NE*) | 1.0 | <0.001 |
| IB-IIB | 53 | 72% | NR (3.7-NR) | 72% (59-85%) | NE | |
| IIIA-IV | 33 | 36% | 1.6 (0.5-NR) | 37% (19-54%) | NE | |
| Diagnosis | | | | | | |
| Clear Cell | 3 | 33% | 3.7 (1.6-NR) | 67% (13-100%) | 1.0 | |
| Endometrioid | 70 | 70% | NR | 72% (61-83%) | 0.58 (0.14-2.5) | <0.001 |
| Serous | 8 | 75% | 1.9 (NE) | 42% (0-100%) | 0.59 (0.08-4.3) | |
| Other | 14 | 21% | 0.7 (0.1-1.5) | 9% (0-26%) | 3.4 (0.72-16) | |
| EMP2 | | | | | | |
| (−) | 83 | 67% | NR (3.7-NR) | 68% (57-79%) | 1.0 | 0.004 |
| (+) | 12 | 25% | 1.9 (0.5-1.9) | 22% (0-49%) | 2.9 (1.4-6.2) | |

‡NR: Not reached
*NE: Not Estimable

Variables with p-value <0.05 are considered univariately significant and these variables were then entered into the multivariate analysis model. Multivariate survival analysis was preformed using the Cox proportional hazards model. The final model was determined by using stepwise regression keeping variables with p-values <0.05 (Tables 6 and 7). All statistical analyses were performed using SAS Software (SAS Institute Inc., Cary, N.C.).

TABLE 6

| MULTIVARIATE ANALYSIS OF OVERALL SURVIVAL# | | | |
|---|---|---|---|
| Variable | | Hazard Ratio (95% CI) | p-value |
| PR | (−) | 1.00 | 0.04 |
| | (+) | 0.28 (0.08-0.94) | |
| Vascular | N | 1.00 | 0.002 |
| | Y | 3.6 (1.6-8.1) | |
| Diagnosis | Clear Cell | 1.00 | 0.03 |
| | Endometrioid | 0.94 (0.12-7.5) | |
| | Serous | 0.56 (0.03-9.6) | |
| | Other | 3.1 (0.34-28) | |

All of the variables are statistically significant, however when entered into a multivariate model the three that remain significant are PR, Vascular, and Diagnosis. EMP2 is no longer significant when entered with these variables.

TABLE 7

| MULTIVARIATE ANALYSIS OF DISEASE FREE SURVIVAL¥ | | | |
|---|---|---|---|
| Variable | | Hazard Ratio (95% CI) | p-value |
| Stage | IA | 1.00 | 0.01 |
| | IB-IIB | NE* | |
| | IIA-IV | NE | |
| Diagnosis | Clear Cell | 1.00 | 0.001 |
| | Endometrioid | 0.36 (0.08-1.6) | |
| | Serous | 0.39 (0.05-2.8) | |
| | Other | 1.7 (0.36-7.7) | |
| EMP2 | (−) | 1.0 | 0.02 |
| | (+) | 2.6 (1.2-5.6) | |

*NE: Not Estimable
¥All of the variables are statistically significant, however when entered into a multivariate model the three that remain significant are PR, Diagnosis, and EMP2.

EMP2 (+) tumors were numerically (but not significantly) increased as a percent of higher stage patients (58%) than EMP2 (−) patients (37%). From the Kaplan-Meier estimates, there was a significant difference in survival status for EMP2 (+) and (−) p=0.06. Likewise, there was significant difference in disease status (p=0.004). When EMP2 was entered into a multivariate overall survival model, this was no longer significant (Table 6). Those variables that remained significant were ER expression, diagnosis, and vascular involvement. EMP2 remained significant in a multivariate disease-free survival model with stage and diagnosis (Table 7).

These results show that EMP2 expression can function as a biomarker for endometrial cancer, both as a surrogate for established clinical disease parameters (ER expression, tumor category, and vascular involvement), and as an independent marker refining prediction of disease-free survival regardless of stage and diagnosis.

Example 2

Phage Display Generated Antibodies

Phage display, first established by Smith et al in 1985, has provided an in vitro immune system which can be used to create high affinity antibodies to virtually any antigens with a bare minimal recognition region (Bradbury, A. R & Marks, J. D., J Immunol Methods (2004) 290:29-49; Marks, J. D. & Bradbury, A., Methods Mol Biol (2004) 248:161-76; Pavlik, P. et al., Hum Antibodies (2003) 12:99-112; Persic, L. et al., FEBS Lett (1999) 443:112-6; Smith, G. P., Science (1985) 228:1315-7). Selection of antibody using phase antibody libraries with filamentous phase and phagemids mimics humoral immune system that lack cell-mediated responses. Thus, generation of purified antibodies with affinities comparable to ones made by conventional hybridoma technology can be achieved without complications such as self-tolerance, T cell help and antigen presentation (Bradbury, A. R. & Marks, J. D., J Immunol Methods (2004) 290:29-49; Pavlik, P. et al., Hum Antibodies (2003) 12:99-112).

For the selection of antibodies against mouse and human epithelial membrane protein-2 (mEMP2 and hEMP2 respectively), a purified phage antibody library expressing a single chain Fv(scFv) with the two V regions linked with a flexible linker was used (Bird, R. E. & Walker, B. W., Trends Biotechnol (1991) 9:132-7; Huston, J. S. et al., Proc Natl Acad Sci USA (1988) 85:5879-83). V genes were derived from naturally rearranged V regions found in B-cells and scFv is expressed on pIII, a bacteriophage coat protein.

20 amino acid sequences from the extracellular loop of mEMP2 and hEMP2 that were previously used for polyclonal antibody production were chosen for antigen targets for the phage display (Wang, C. X. et al., Blood (2001) 97:3890-5). Successful scFv isolation against 20-mer peptide has been previously reported (Persic, L. et al., FEES Lett (1999) 443: 112-6; Griffiths, A. D. et al., Embo J (1993) 12:725-34), in order to maintain natural conformation, these peptides were biotinylated at C- and N-termini with 4 amino acid long linkers (GSGS (SEQ ID NO:2)). 3 rounds of selection using streptavidin and avidin-coated beads were carried out for each sample to isolate high affinity antibodies as previously described (Marks, J. D. & Bradbury, A., Methods Mol Biol (2004) 248:161-76). Input and output concentrations of phage antibody libraries and values for recovery and enrichment for each round are calculated and shown below (Tables 8-11

TABLE 8

| N-termini (human) (N-hEMP2) | | | |
|---|---|---|---|
| | R1 | R2 | R3 |
| Input | $10^{12}$ | $10^{12}$ | $3 \times 10^{11}$ |
| Output | $10^{7}$ | $1.1 \times 10^{8}$ | $7.8 \times 10^{8}$ |
| Recovery | $10^{-5}$ | $1.1 \times 10^{-4}$ | $2.6 \times 10^{-3}$ |
| Enrichment | | 11 | 23.6 |

TABLE 9

| C-termini (human) (C-hEMP2) | | | |
|---|---|---|---|
| | R1 | R2 | R3 |
| Input | $10^{12}$ | $10^{12}$ | $2 \times 10^{11}$ |
| Output | $10^{7}$ | $8 \times 10^{7}$ | $2.1 \times 10^{8}$ |
| Recovery | $10^{-5}$ | $8 \times 10^{-5}$ | $1.1 \times 10^{-3}$ |
| Enrichment | | 8 | 13.1 |

TABLE 10

| N-termini (mouse) (N-mEMP2) | | | |
|---|---|---|---|
| | R1 | R2 | R3 |
| Input | $10^{12}$ | $1.8 \times 10^{10}$ | $3.4 \times 10^{13}$ |
| Output | $6 \times 10^{5}$ | $10^{4}$ | $3.6 \times 10^{8}$ |
| Recovery | $6 \times 10^{-7}$ | $5.6 \times 10^{-7}$ | $1.1 \times 10^{-5}$ |
| Enrichment | | 0.9 | 19.0 |

TABLE 11

| C-termini (mouse) (C-mEMP2) | | | |
|---|---|---|---|
| | R1 | R2 | R3 |
| Input | $10^{12}$ | $7.5 \times 10^{9}$ | $6.5 \times 10^{12}$ |
| Output | $2 \times 10^{7}$ | $5.2 \times 10^{6}$ | $7.0 \times 10^{5}$ |
| Recovery | $2 \times 10^{-5}$ | $2.7 \times 10^{-4}$ | $1.1 \times 10^{-7}$ |
| Enrichment | | 13.5 | $4 \times 10^{-4}$ |

Figure 11:
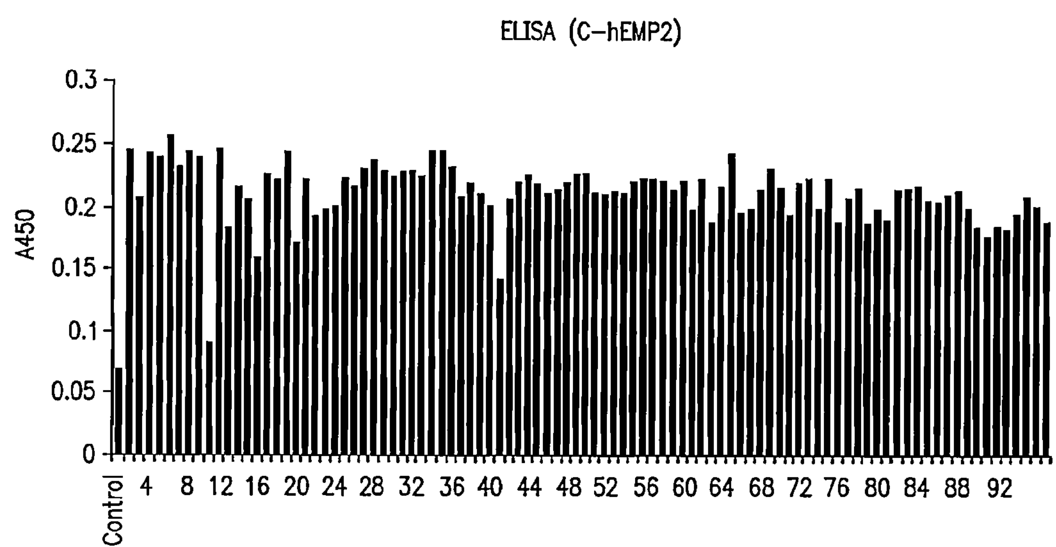
FIG. 11 shows results from ELISA analysis of C-termini-biotinylated human single chain Fv (scFv) peptides directed against EMP2.
Figure 12:
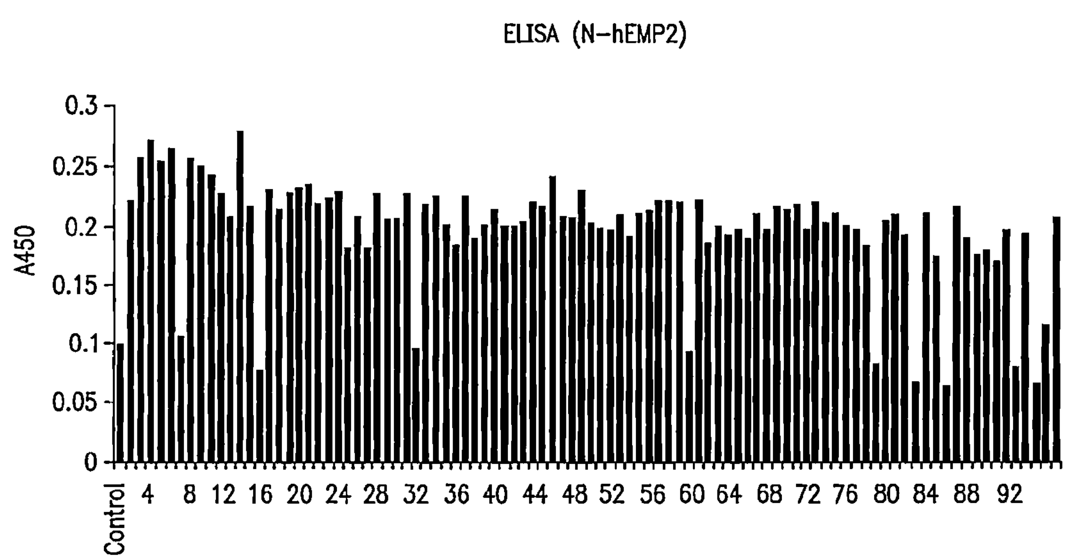
FIG. 12 shows results from ELISA analysis of N-termini-biotinylated human scFv peptides directed against EMP2.
Figure 13:
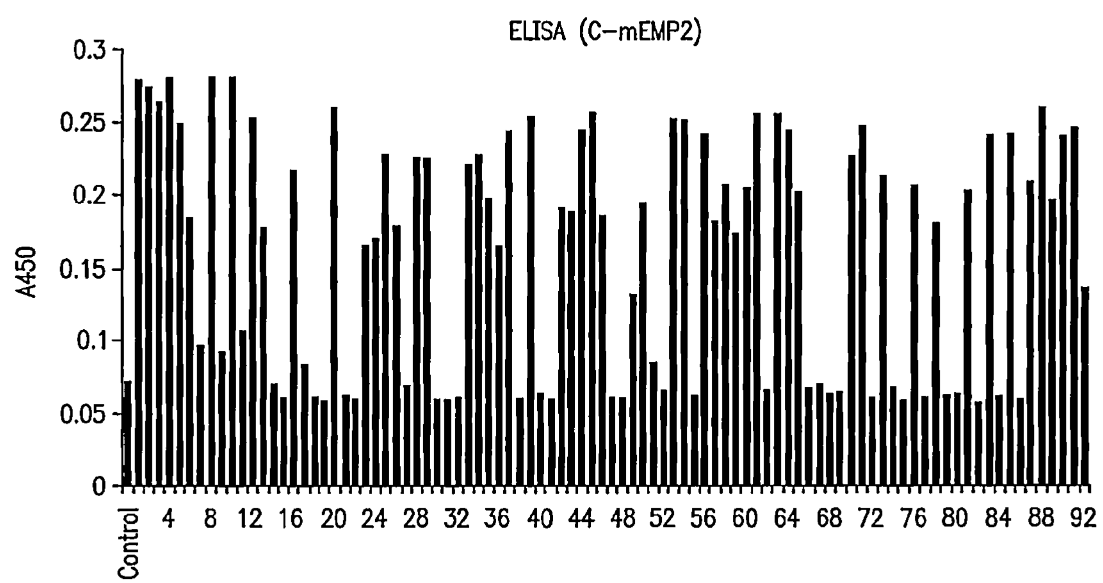
FIG. 13 shows results from ELISA analysis of C-termini-biotinylated mouse scFv peptides directed against EMP2.

Specificity of selected antibodies were tested by ELISA, in which 95 colonies picked from the isolated phage populations were incubated with bound mEMP2/hEMP2 peptides on streptavidin coated plates (FIGS. 11-13). Most of colonies showed a 4-5 fold increase in reactivity compared to control, indicating their high specificity against antigens. N-mEMP2 samples failed to show high reactivity, only C-mEMF2 samples were used for further identification of anti-mEMP2 antibodies.

Of these highly reactive colonies, 14 colonies/sample were chosen for DNA fingerprinting and subsequent DNA sequence analysis. There were three unique sequences found in hEMP2 antibodies and five were found in mEMP2 antibodies. Protein expression and purification system have been developed for each antibody using His containing expression vectors (such vectors are well known in art and are available commercially).

Figure 14A:
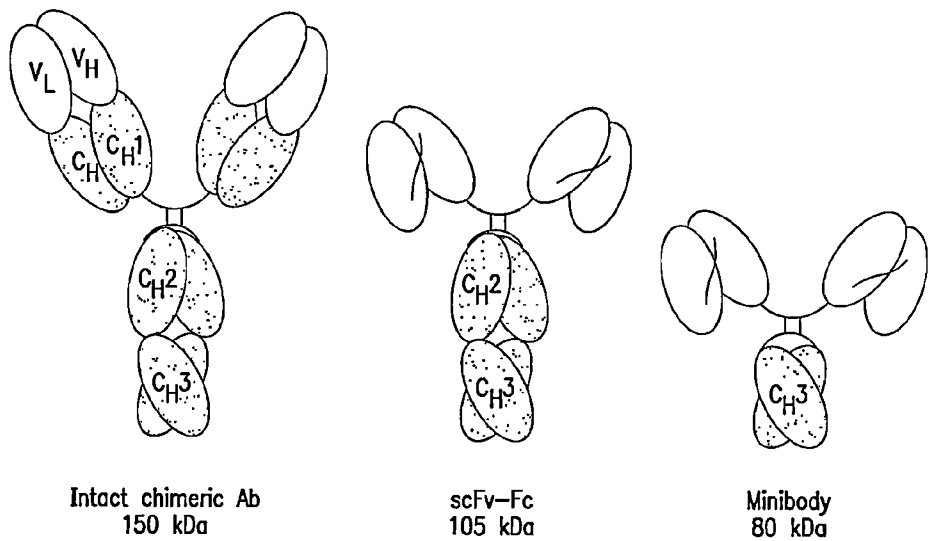
FIG. 14A depicts an intact chimeric antibody, a scFv-Fc antibody, and a minibody.
Figure 14B:
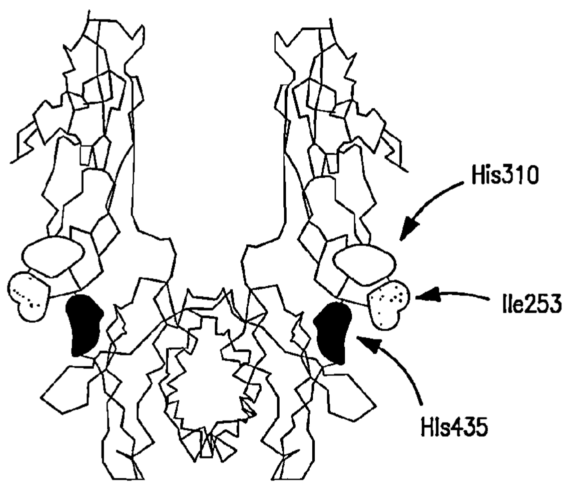
FIG. 14B depicts a backbone drawing of a chimeric antibody.
Figure 14C:
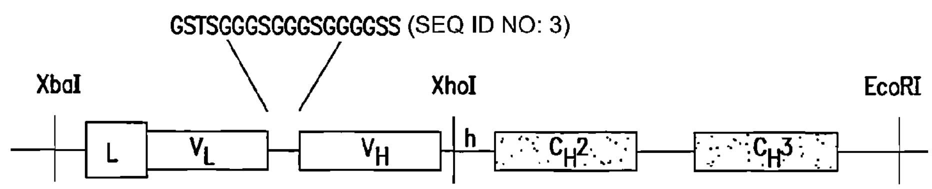
FIG. 14C depicts the insertion of SEQ ID NO:3 into an intact Fc region containing $V_L$, $V_H$, $C_H2$, and $C_H3$ domains to produce an intact chimeric antibody.

The scFvs can be fused to intact Fe region containing $C_H1$, $C_H2$ and/or $C_H3$ domains to produce intact chimeric antibody (Kenanova, V. et al., Cancer Res (2005) 65:622-31). (See, e.g., FIG. 14).

Such Fc-fused antibodies not only stabilize the antibodies, almost to a degree to natural antibodies (Slavin-Chiorini, D.C. et al., Cancer Res (1995) 55:5957s-5967s; Xu, X. et al., Cancer Res (2000) 60:4475-84), but also allows detection of antibodies with anti-Fc secondary antibodies conjugated with detectable markers. Thus, such antibodies provide strong biochemical and therapeutic tools by producing highly purified stable anti-EMP2 antibodies with increased specificity.

All references recited are herein incorporated by reference, in their entirety. Further, although the invention has been described with reference to the above examples, it will be understood that modifications and variations are encompassed within the spirit and scope of the invention. Accordingly, the invention is limited only by the following claims.

We claim:

1. A method for determining the likelihood of a non-cancerous endometrial cell becoming cancerous, comprising:

determining the level of expression of epithelial membrane protein 2 (EMP2) in a test sample comprising the non-cancerous endometrial cell, wherein increased levels of expression of EMP2 in the non-cancerous endometrial cell relative to a control level correlates with the endometrial cell having an increased likelihood of becoming cancerous, wherein the level of expression is determined using an anti-epithelial membrane protein 2 (EMP2) antibody or antigen binding fragment thereof that binds to the amino acid sequence as set forth in SEQ ID NO: 1.

2. The method of claim 1, wherein the determining comprises performing Western blotting, protein gel electrophoresis, immunoprecipitation, ELISA, and/or immunohistochemistry.

3. The method of claim 2, comprising performing immunohistochemistry on a group of non-cancerous endometrial cells using the anti-epithelial membrane protein 2 (EMP2) antibody or antigen binding fragment thereof; and determining the binding of the antibody or antigen binding fragment thereof to the non-cancerous endometrial cells, wherein an increased amount of antibody or antigen-binding fragment thereof bound to the non-cancerous endometrial cells relative to a control level correlates with the non-cancerous endometrial cells having an increased likelihood of becoming cancerous.

* * * * *